ical Society 134(29):12308-12318, Jul. 2012 (Author Manuscript).

(12) United States Patent
Kawaguchi et al.

(10) Patent No.: US 11,001,819 B2
(45) Date of Patent: May 11, 2021

(54) ENDOS MUTANT ENZYME

(71) Applicant: Daiichi Sankyo Company, Limited, Tokyo (JP)

(72) Inventors: Yoshirou Kawaguchi, Shinagawa-ku (JP); Kensuke Nakamura, Shinagawa-ku (JP); Yukiko Sekiguchi, Shinagawa-ku (JP); Mitsuhiro Iwamoto, Shinagawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 193 days.

(21) Appl. No.: 15/745,357

(22) PCT Filed: Jul. 15, 2016

(86) PCT No.: PCT/JP2016/070921
§ 371 (c)(1),
(2) Date: Jan. 16, 2018

(87) PCT Pub. No.: WO2017/010559
PCT Pub. Date: Jan. 19, 2017

(65) Prior Publication Data
US 2018/0208915 A1    Jul. 26, 2018

(30) Foreign Application Priority Data
Jul. 16, 2015  (JP) .............. JP2015-141901

(51) Int. Cl.
*C12N 9/24* (2006.01)
*C12P 21/02* (2006.01)
*C12N 15/09* (2006.01)
*C12N 15/02* (2006.01)
*C07K 16/32* (2006.01)

(52) U.S. Cl.
CPC ............ *C12N 9/2402* (2013.01); *C07K 16/32* (2013.01); *C12N 15/02* (2013.01); *C12N 15/09* (2013.01); *C12P 21/02* (2013.01); *C12Y 302/01096* (2013.01); *C07K 2317/41* (2013.01)

(58) Field of Classification Search
None
See application file for complete search history.

(56) References Cited

U.S. PATENT DOCUMENTS

2015/0087814 A1    3/2015  Wang et al.
2015/0125443 A1*   5/2015  Crispin ............ A61K 39/39558
                                              424/133.1

FOREIGN PATENT DOCUMENTS

JP    2015-507925 A    3/2015

OTHER PUBLICATIONS

Huang, W., et al., "Chemoenzymatic Glycoengineering of Intact IgG Antibodies for Gain of Functions," Journal of the American Chemical Society 134(29):12308-12318, Jul. 2012 (Author Manuscript).
International Search Report and Written Opinion dated Sep. 6, 2016, issued in International Application No. PCT/JP2016/070921, filed Jul. 15, 2016, 10 pages.

* cited by examiner

*Primary Examiner* — Paul J Holland
(74) *Attorney, Agent, or Firm* — Christensen O'Connor Johnson Kindness PLLC

(57) ABSTRACT

The present invention provides an EndoS mutant enzyme having an amino acid sequence of EndoS D233Q and further having a particular additional mutation and exhibiting a reduced hydrolysis activity, in comparison with the activity of EndoS D233Q, to an N-linked sugar chain (N297-linked sugar chain) linked to Asn at position 297 in IgG and a gene encoding the same.

14 Claims, 9 Drawing Sheets
Specification includes a Sequence Listing.

[Figure 1]
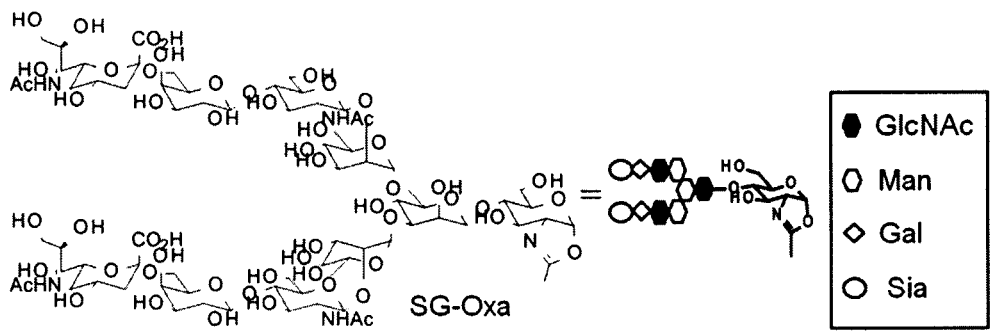
[Figure 2]
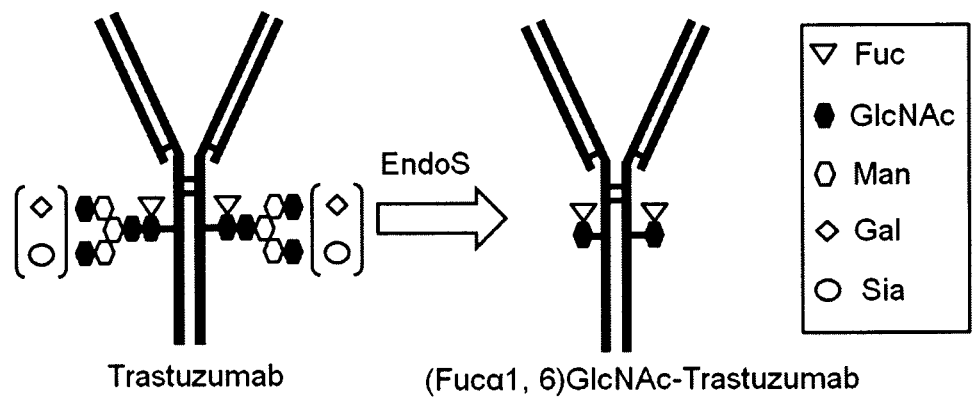
[Figure 3]
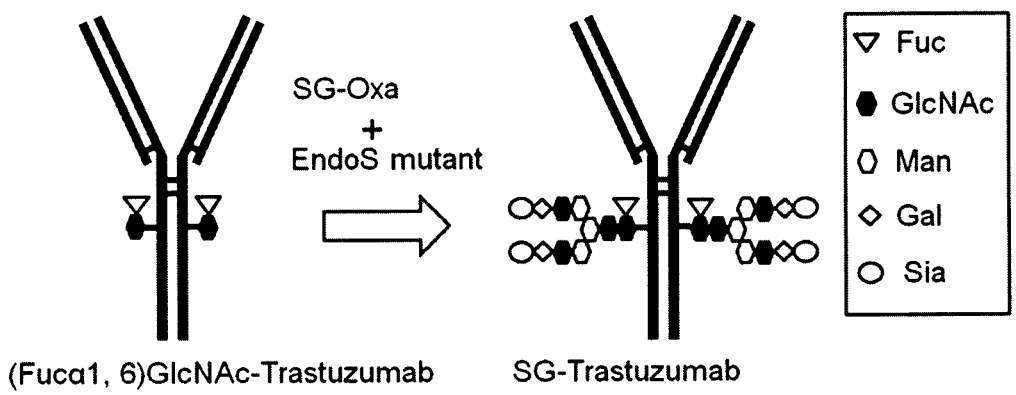

[Figure 4-1]

|  | 37 | 40 | | | | 50 | | | | | 60 | | | | | 70 | |  |
|---|---|---|---|---|---|---|---|---|---|---|---|---|---|---|---|---|---|---|
| EndoS D233Q             | E E K T V Q V Q K G L P S I D S L H Y L S E N S K K E F K E E L S K A | 71 |
| EndoS D233Q/Q303L       | E E K T V Q V Q K G L P S I D S L H Y L S E N S K K E F K E E L S K A | 71 |
| EndoS D233Q/Q303L/E350Q | E E K T V Q V Q K G L P S I D S L H Y L S E N S K K E F K E E L S K A | 71 |
| EndoS D233Q/Q303L/D405A | E E K T V Q V Q K G L P S I D S L H Y L S E N S K K E F K E E L S K A | 71 |
| EndoS D233Q/E350Q       | E E K T V Q V Q K G L P S I D S L H Y L S E N S K K E F K E E L S K A | 71 |
| EndoS D233Q/D405A       | E E K T V Q V Q K G L P S I D S L H Y L S E N S K K E F K E E L S K A | 71 |
| EndoS D233Q/Y402F       | E E K T V Q V Q K G L P S I D S L H Y L S E N S K K E F K E E L S K A | 71 |

|  | | | 80 | | | | | 90 | | | | | 100 | | | | | | |
|---|---|---|---|---|---|---|---|---|---|---|---|---|---|---|---|---|---|---|
| EndoS D233Q             | G Q E S Q K V K E I L A K K A Q Q A D K Q A D K M K I P E K I P M | 106 |
| EndoS D233Q/Q303L       | G Q E S Q K V K E I L A K K A Q Q A D K Q A D K M K I P E K I P M | 106 |
| EndoS D233Q/Q303L/E350Q | G Q E S Q K V K E I L A K K A Q Q A D K Q A D K M K I P E K I P M | 106 |
| EndoS D233Q/Q303L/D405A | G Q E S Q K V K E I L A K K A Q Q A D K Q A D K M K I P E K I P M | 106 |
| EndoS D233Q/E350Q       | G Q E S Q K V K E I L A K K A Q Q A D K Q A D K M K I P E K I P M | 106 |
| EndoS D233Q/D405A       | G Q E S Q K V K E I L A K K A Q Q A D K Q A D K M K I P E K I P M | 106 |
| EndoS D233Q/Y402F       | G Q E S Q K V K E I L A K K A Q Q A D K Q A D K M K I P E K I P M | 106 |

|  | | 110 | | | | | 120 | | | | | 130 | | | | | 140 | | |
|---|---|---|---|---|---|---|---|---|---|---|---|---|---|---|---|---|---|---|
| EndoS D233Q             | K P L H G P L Y G G Y F R T W H D K T S D P T E K D K V N S M G E L P | 141 |
| EndoS D233Q/Q303L       | K P L H G P L Y G G Y F R T W H D K T S D P T E K D K V N S M G E L P | 141 |
| EndoS D233Q/Q303L/E350Q | K P L H G P L Y G G Y F R T W H D K T S D P T E K D K V N S M G E L P | 141 |
| EndoS D233Q/Q303L/D405A | K P L H G P L Y G G Y F R T W H D K T S D P T E K D K V N S M G E L P | 141 |
| EndoS D233Q/E350Q       | K P L H G P L Y G G Y F R T W H D K T S D P T E K D K V N S M G E L P | 141 |
| EndoS D233Q/D405A       | K P L H G P L Y G G Y F R T W H D K T S D P T E K D K V N S M G E L P | 141 |
| EndoS D233Q/Y402F       | K P L H G P L Y G G Y F R T W H D K T S D P T E K D K V N S M G E L P | 141 |

|  | | 150 | | | | | 160 | | | | | 170 | | | | | | |
|---|---|---|---|---|---|---|---|---|---|---|---|---|---|---|---|---|---|---|
| EndoS D233Q             | K E V D L A F I F H D W T K D Y S L F W K K E L A T K K H V P K L N K Q G | 176 |
| EndoS D233Q/Q303L       | K E V D L A F I F H D W T K D Y S L F W K K E L A T K K H V P K L N K Q G | 176 |
| EndoS D233Q/Q303L/E350Q | K E V D L A F I F H D W T K D Y S L F W K K E L A T K K H V P K L N K Q G | 176 |
| EndoS D233Q/Q303L/D405A | K E V D L A F I F H D W T K D Y S L F W K K E L A T K K H V P K L N K Q G | 176 |
| EndoS D233Q/E350Q       | K E V D L A F I F H D W T K D Y S L F W K K E L A T K K H V P K L N K Q G | 176 |
| EndoS D233Q/D405A       | K E V D L A F I F H D W T K D Y S L F W K K E L A T K K H V P K L N K Q G | 176 |
| EndoS D233Q/Y402F       | K E V D L A F I F H D W T K D Y S L F W K K E L A T K K H V P K L N K Q G | 176 |

[Figure 4-2]

```
                          180        190        200        210
EndoS D2330               TRVIRTIIPWRFLAGGDNSGIAEDTSKYPNTPEGNK  211
EndoS D233Q/Q303L         TRVIRTIIPWRFLAGGDNSGIAEDTSKYPNTPEGNK  211
EndoS D233Q/Q303L/E350Q   TRVIRTIIPWRFLAGGDNSGIAEDTSKYPNTPEGNK  211
EndoS D233Q/Q303L/D405A   TRVIRTIIPWRFLAGGDNSGIAEDTSKYPNTPEGNK  211
EndoS D233Q/E350Q         TRVIRTIIPWRFLAGGDNSGIAEDTSKYPNTPEGNK  211
EndoS D233Q/D405A         TRVIRTIIPWRFLAGGDNSGIAEDTSKYPNTPEGNK  211
EndoS D233Q/Y402F         TRVIRTIIPWRFLAGGDNSGIAEDTSKYPNTPEGNK  211

220        230        240
EndoS D233Q               ALAKAIVDEYVVYKYNLDDVQVEHDSIPKVDKKE  246
EndoS D233Q/Q303L         ALAKAIVDEYVVYKYNLDDVQVEHDSIPKVDKKE  246
EndoS D233Q/Q303L/E350Q   ALAKAIVDEYVVYKYNLDDVQVEHDSIPKVDKKE  246
EndoS D233Q/Q303L/D405A   ALAKAIVDEYVVYKYNLDDVQVEHDSIPKVDKKE  246
EndoS D233Q/E350Q         ALAKAIVDEYVVYKYNLDDVQVEHDSIPKVDKKE  246
EndoS D233Q/D405A         ALAKAIVDEYVVYKYNLDDVQVEHDSIPKVDKKE  246
EndoS D233Q/Y402F         ALAKAIVDEYVVYKYNLDDVQVEHDSIPKVDKKE  246

250        260        270        280
EndoS D233Q               DTAGVERSIQVFEEIGKLIIGPKGVDKSRLFIMDST  281
EndoS D233Q/Q303L         DTAGVERSIQVFEEIGKLIIGPKGVDKSRLFIMDST  281
EndoS D233Q/Q303L/E350Q   DTAGVERSIQVFEEIGKLIIGPKGVDKSRLFIMDST  281
EndoS D233Q/Q303L/D405A   DTAGVERSIQVFEEIGKLIIGPKGVDKSRLFIMDST  281
EndoS D233Q/E350Q         DTAGVERSIQVFEEIGKLIIGPKGVDKSRLFIMDST  281
EndoS D233Q/D405A         DTAGVERSIQVFEEIGKLIIGPKGVDKSRLFIMDST  281
EndoS D233Q/Y402F         DTAGVERSIQVFEEIGKLIIGPKGVDKSRLFIMDST  281

290        300        310
EndoS D233Q               YMADKNPLIERGAPYIINLLLVQVYGSQGEKGGWEP  316
EndoS D233Q/Q303L         YMADKNPLIERGAPYIINLLLVLVYGSQGEKGGWEP  316
EndoS D233Q/Q303L/E350Q   YMADKNPLIERGAPYIINLLLVLVYGSQGEKGGWEP  316
EndoS D233Q/Q303L/D405A   YMADKNPLIERGAPYIINLLLVLVYGSQGEKGGWEP  316
EndoS D233Q/E350Q         YMADKNPLIERGAPYIINLLLVQVYGSQGEKGGWEP  316
EndoS D233Q/D405A         YMADKNPLIERGAPYIINLLLVQVYGSQGEKGGWEP  316
EndoS D233Q/Y402F         YMADKNPLIERGAPYIINLLLVQVYGSQGEKGGWEP  316
```

[Figure 4-3]

```
                     320         330         340         350
EndoS D233Q           VSNRPEKTMEERWQGYSKYIRPEQYMIGFSFYEEN     351
EndoS D233Q/Q303L     VSNRPEKTMEERWQGYSKYIRPEQYMIGFSFYEEN     351
EndoS D233Q/Q303L/E350Q VSNRPEKTMEERWQGYSKYIRPEQYMIGFSFYEQN   351
EndoS D233Q/Q303L/D405A VSNRPEKTMEERWQGYSKYIRPEQYMIGFSFYEEN   351
EndoS D233Q/E350Q     VSNRPEKTMEERWQGYSKYIRPEQYMIGFSFYEQN     351
EndoS D233Q/D405A     VSNRPEKTMEERWQGYSKYIRPEQYMIGFSFYEEN     351
EndoS D233Q/Y402F     VSNRPEKTMEERWQGYSKYIRPEQYMIGFSFYEEN     351

360         370         380
EndoS D233Q           AQEGNLWYDINSRKDEDKANGINTDIHTGTRAERYA     386
EndoS D233Q/Q303L     AQEGNLWYDINSRKDEDKANGINTDIHTGTRAERYA     386
EndoS D233Q/Q303L/E350Q AQEGNLWYDINSRKDEDKANGINTDIHTGTRAERYA   386
EndoS D233Q/Q303L/D405A AQEGNLWYDINSRKDEDKANGINTDIHTGTRAERYA   386
EndoS D233Q/E350Q     AQEGNLWYDINSRKDEDKANGINTDIHTGTRAERYA     386
EndoS D233Q/D405A     AQEGNLWYDINSRKDEDKANGINTDIHTGTRAERYA     386
EndoS D233Q/Y402F     AQEGNLWYDINSRKDEDKANGINTDIHTGTRAERYA     386

390         400         410         420
EndoS D233Q           RWQPKTGGVKGGIFSYAIDRDGVAHQPKKKYAAKQKE    421
EndoS D233Q/Q303L     RWQPKTGGVKGGIFSYAIDRDGVAHQPKKKYAAKQKE    421
EndoS D233Q/Q303L/E350Q RWQPKTGGVKGGIFSYAIDRDGVAHQPKKKYAAKQKE  421
EndoS D233Q/Q303L/D405A RWQPKTGGVKGGIFSYAIARDGVAHQPKKKYAAKQKE  421
EndoS D233Q/E350Q     RWQPKTGGVKGGIFSYAIDRDGVAHQPKKKYAAKQKE    421
EndoS D233Q/D405A     RWQPKTGGVKGGIFSYAIARDGVAHQPKKKYAAKQKE    421
EndoS D233Q/Y402F     RWQPKTGGVKGGIFSFAIDRDGVAHQPKKKYAAKQKE    421

430         440         450
EndoS D233Q           FKDATDNIFHSDYSVSKALKTVMLKDKSYDLIDEK      456
EndoS D233Q/Q303L     FKDATDNIFHSDYSVSKALKTVMLKDKSYDLIDEK      456
EndoS D233Q/Q303L/E350Q FKDATDNIFHSDYSVSKALKTVMLKDKSYDLIDEK    456
EndoS D233Q/Q303L/D405A FKDATDNIFHSDYSVSKALKTVMLKDKSYDLIDEK    456
EndoS D233Q/E350Q     FKDATDNIFHSDYSVSKALKTVMLKDKSYDLIDEK      456
EndoS D233Q/D405A     FKDATDNIFHSDYSVSKALKTVMLKDKSYDLIDEK      456
EndoS D233Q/Y402F     FKDATDNIFHSDYSVSKALKTVMLKDKSYDLIDEK      456
```

[Figure 4-4]

|  | 460 | 470 | 480 | 490 |  |
|---|---|---|---|---|---|
| EndoS D233Q                | DFPDKALREAVMAQVGTRKGDLERFNGTLRLDNPA | 491 |
| EndoS D233Q/Q303L           | DFPDKALREAVMAQVGTRKGDLERFNGTLRLDNPA | 491 |
| EndoS D233Q/Q303L/E350Q     | DFPDKALREAVMAQVGTRKGDLERFNGTLRLDNPA | 491 |
| EndoS D233Q/Q303L/D405A     | DFPDKALREAVMAQVGTRKGDLERFNGTLRLDNPA | 491 |
| EndoS D233Q/E350Q           | DFPDKALREAVMAQVGTRKGDLERFNGTLRLDNPA | 491 |
| EndoS D233Q/D405A           | DFPDKALREAVMAQVGTRKGDLERFNGTLRLDNPA | 491 |
| EndoS D233Q/Y402F           | DFPDKALREAVMAQVGTRKGDLERFNGTLRLDNPA | 491 |

|  | 500 | 510 | 520 |  |
|---|---|---|---|---|
| EndoS D233Q                | IQSLEGLNKFKKKLAQLDLIIGLSRITTKLDRSVLPAN | 526 |
| EndoS D233Q/Q303L           | IQSLEGLNKFKKKLAQLDLIIGLSRITTKLDRSVLPAN | 526 |
| EndoS D233Q/Q303L/E350Q     | IQSLEGLNKFKKKLAQLDLIIGLSRITTKLDRSVLPAN | 526 |
| EndoS D233Q/Q303L/D405A     | IQSLEGLNKFKKKLAQLDLIIGLSRITTKLDRSVLPAN | 526 |
| EndoS D233Q/E350Q           | IQSLEGLNKFKKKLAQLDLIIGLSRITTKLDRSVLPAN | 526 |
| EndoS D233Q/D405A           | IQSLEGLNKFKKKLAQLDLIIGLSRITTKLDRSVLPAN | 526 |
| EndoS D233Q/Y402F           | IQSLEGLNKFKKKLAQLDLIIGLSRITTKLDRSVLPAN | 526 |

|  | 530 | 540 | 550 | 560 |  |
|---|---|---|---|---|---|
| EndoS D233Q                | MKPGKDTTLLETVLETYKKDNKEEPATIIPPVSLKVSG | 561 |
| EndoS D233Q/Q303L           | MKPGKDTTLLETVLETYKKDNKEEPATIIPPVSLKVSG | 561 |
| EndoS D233Q/Q303L/E350Q     | MKPGKDTTLLETVLETYKKDNKEEPATIIPPVSLKVSG | 561 |
| EndoS D233Q/Q303L/D405A     | MKPGKDTTLLETVLETYKKDNKEEPATIIPPVSLKVSG | 561 |
| EndoS D233Q/E350Q           | MKPGKDTTLLETVLETYKKDNKEEPATIIPPVSLKVSG | 561 |
| EndoS D233Q/D405A           | MKPGKDTTLLETVLETYKKDNKEEPATIIPPVSLKVSG | 561 |
| EndoS D233Q/Y402F           | MKPGKDTTLLETVLETYKKDNKEEPATIIPPVSLKVSG | 561 |

|  | 570 | 580 | 590 |  |
|---|---|---|---|---|
| EndoS D233Q                | LTGLKELDLSGFDRETLAGLDAATLTSLEKVDHISSG | 596 |
| EndoS D233Q/Q303L           | LTGLKELDLSGFDRETLAGLDAATLTSLEKVDHISSG | 596 |
| EndoS D233Q/Q303L/E350Q     | LTGLKELDLSGFDRETLAGLDAATLTSLEKVDHISSG | 596 |
| EndoS D233Q/Q303L/D405A     | LTGLKELDLSGFDRETLAGLDAATLTSLEKVDHISSG | 596 |
| EndoS D233Q/E350Q           | LTGLKELDLSGFDRETLAGLDAATLTSLEKVDHISSG | 596 |
| EndoS D233Q/D405A           | LTGLKELDLSGFDRETLAGLDAATLTSLEKVDHISSG | 596 |
| EndoS D233Q/Y402F           | LTGLKELDLSGFDRETLAGLDAATLTSLEKVDHISSG | 596 |

[Figure 4-5]

| | | 600 | | 610 | | 620 | | 630 | |
|---|---|---|---|---|---|---|---|---|---|
| EndoS D233Q | N K | L D L A P G T E N R Q I F D T M L S T I S N H V G S N E Q T V K F | 631 |
| EndoS D233Q/Q303L | N K | L D L A P G T E N R Q I F D T M L S T I S N H V G S N E Q T V K F | 631 |
| EndoS D233Q/Q303L/E350Q | N K | L D L A P G T E N R Q I F D T M L S T I S N H V G S N E Q T V K F | 631 |
| EndoS D233Q/Q303L/D405A | N K | L D L A P G T E N R Q I F D T M L S T I S N H V G S N E Q T V K F | 631 |
| EndoS D233Q/E350Q | N K | L D L A P G T E N R Q I F D T M L S T I S N H V G S N E Q T V K F | 631 |
| EndoS D233Q/D405A | N K | L D L A P G T E N R Q I F D T M L S T I S N H V G S N E Q T V K F | 631 |
| EndoS D233Q/Y402F | N K | L D L A P G T E N R Q I F D T M L S T I S N H V G S N E Q T V K F | 631 |

| | 640 | 650 | 660 | |
|---|---|---|---|---|
| EndoS D233Q | D K Q K P T G H Y P D T Y G K T S L R L P V A N E K V D L Q S Q L L F | 666 |
| EndoS D233Q/Q303L | D K Q K P T G H Y P D T Y G K T S L R L P V A N E K V D L Q S Q L L F | 666 |
| EndoS D233Q/Q303L/E350Q | D K Q K P T G H Y P D T Y G K T S L R L P V A N E K V D L Q S Q L L F | 666 |
| EndoS D233Q/Q303L/D405A | D K Q K P T G H Y P D T Y G K T S L R L P V A N E K V D L Q S Q L L F | 666 |
| EndoS D233Q/E350Q | D K Q K P T G H Y P D T Y G K T S L R L P V A N E K V D L Q S Q L L F | 666 |
| EndoS D233Q/D405A | D K Q K P T G H Y P D T Y G K T S L R L P V A N E K V D L Q S Q L L F | 666 |
| EndoS D233Q/Y402F | D K Q K P T G H Y P D T Y G K T S L R L P V A N E K V D L Q S Q L L F | 666 |

| | 670 | 680 | 690 | 700 | |
|---|---|---|---|---|---|
| EndoS D233Q | G T V T N Q G T L I I N S E A D Y K K A Y Q N H K I A G R S F V D S N Y H | 701 |
| EndoS D233Q/Q303L | G T V T N Q G T L I I N S E A D Y K K A Y Q N H K I A G R S F V D S N Y H | 701 |
| EndoS D233Q/Q303L/E350Q | G T V T N Q G T L I I N S E A D Y K K A Y Q N H K I A G R S F V D S N Y H | 701 |
| EndoS D233Q/Q303L/D405A | G T V T N Q G T L I I N S E A D Y K K A Y Q N H K I A G R S F V D S N Y H | 701 |
| EndoS D233Q/E350Q | G T V T N Q G T L I I N S E A D Y K K A Y Q N H K I A G R S F V D S N Y H | 701 |
| EndoS D233Q/D405A | G T V T N Q G T L I I N S E A D Y K K A Y Q N H K I A G R S F V D S N Y H | 701 |
| EndoS D233Q/Y402F | G T V T N Q G T L I I N S E A D Y K K A Y Q N H K I A G R S F V D S N Y H | 701 |

| | 710 | 720 | 730 | |
|---|---|---|---|---|
| EndoS D233Q | Y N N F K V S Y E N Y T T V K V T D S T L G T T T D K T L A T D K E E T | 736 |
| EndoS D233Q/Q303L | Y N N F K V S Y E N Y T T V K V T D S T L G T T T D K T L A T D K E E T | 736 |
| EndoS D233Q/Q303L/E350Q | Y N N F K V S Y E N Y T T V K V T D S T L G T T T D K T L A T D K E E T | 736 |
| EndoS D233Q/Q303L/D405A | Y N N F K V S Y E N Y T T V K V T D S T L G T T T D K T L A T D K E E T | 736 |
| EndoS D233Q/E350Q | Y N N F K V S Y E N Y T T V K V T D S T L G T T T D K T L A T D K E E T | 736 |
| EndoS D233Q/D405A | Y N N F K V S Y E N Y T T V K V T D S T L G T T T D K T L A T D K E E T | 736 |
| EndoS D233Q/Y402F | Y N N F K V S Y E N Y T T V K V T D S T L G T T T D K T L A T D K E E T | 736 |

[Figure 4-6]

|  | 740 | 750 | 760 | 770 |  |
|---|---|---|---|---|---|
| EndoS D233Q                | YKVDFFSPADKT | KAVHTAKV | IVGDEKTMMVN | LAEG | 771 |
| EndoS D233Q/Q303L          | YKVDFFSPADKT | KAVHTAKV | IVGDEKTMMVN | LAEG | 771 |
| EndoS D233Q/Q303L/E350Q    | YKVDFFSPADKT | KAVHTAKV | IVGDEKTMMVN | LAEG | 771 |
| EndoS D233Q/Q303L/D405A    | YKVDFFSPADKT | KAVHTAKV | IVGDEKTMMVN | LAEG | 771 |
| EndoS D233Q/E350Q          | YKVDFFSPADKT | KAVHTAKV | IVGDEKTMMVN | LAEG | 771 |
| EndoS D233Q/D405A          | YKVDFFSPADKT | KAVHTAKV | IVGDEKTMMVN | LAEG | 771 |
| EndoS D233Q/Y402F          | YKVDFFSPADKT | KAVHTAKV | IVGDEKTMMVN | LAEG | 771 |

|  | 780 | 790 | 800 |  |
|---|---|---|---|---|
| EndoS D233Q                | ATVIGGSADPVNARKKVF | DGQLGSETDN | ISLGWDSK | 806 |
| EndoS D233Q/Q303L          | ATVIGGSADPVNARKKVF | DGQLGSETDN | ISLGWDSK | 806 |
| EndoS D233Q/Q303L/E350Q    | ATVIGGSADPVNARKKVF | DGQLGSETDN | ISLGWDSK | 806 |
| EndoS D233Q/Q303L/D405A    | ATVIGGSADPVNARKKVF | DGQLGSETDN | ISLGWDSK | 806 |
| EndoS D233Q/E350Q          | ATVIGGSADPVNARKKVF | DGQLGSETDN | ISLGWDSK | 806 |
| EndoS D233Q/D405A          | ATVIGGSADPVNARKKVF | DGQLGSETDN | ISLGWDSK | 806 |
| EndoS D233Q/Y402F          | ATVIGGSADPVNARKKVF | DGQLGSETDN | ISLGWDSK | 806 |

|  | 810 | 820 | 830 | 840 |  |
|---|---|---|---|---|---|
| EndoS D233Q                | QSIIFKKLKEDG | LIKHHWRFF | NDSARNPETT | NNKPHIQE | 841 |
| EndoS D233Q/Q303L          | QSIIFKKLKEDG | LIKHHWRFF | NDSARNPETT | NNKPHIQE | 841 |
| EndoS D233Q/Q303L/E350Q    | QSIIFKKLKEDG | LIKHHWRFF | NDSARNPETT | NNKPHIQE | 841 |
| EndoS D233Q/Q303L/D405A    | QSIIFKKLKEDG | LIKHHWRFF | NDSARNPETT | NNKPHIQE | 841 |
| EndoS D233Q/E350Q          | QSIIFKKLKEDG | LIKHHWRFF | NDSARNPETT | NNKPHIQE | 841 |
| EndoS D233Q/D405A          | QSIIFKKLKEDG | LIKHHWRFF | NDSARNPETT | NNKPHIQE | 841 |
| EndoS D233Q/Y402F          | QSIIFKKLKEDG | LIKHHWRFF | NDSARNPETT | NNKPHIQE | 841 |

|  | 850 | 860 | 870 |  |
|---|---|---|---|---|
| EndoS D233Q                | ASLQIFNNIKDYNLDDNLLENPNNKFDDDEKYW | ITTVDTY | 876 |
| EndoS D233Q/Q303L          | ASLQIFNNIKDYNLDDNLLENPNNKFDDDEKYW | ITTVDTY | 876 |
| EndoS D233Q/Q303L/E350Q    | ASLQIFNNIKDYNLDDNLLENPNNKFDDDEKYW | ITTVDTY | 876 |
| EndoS D233Q/Q303L/D405A    | ASLQIFNNIKDYNLDDNLLENPNNKFDDDEKYW | ITTVDTY | 876 |
| EndoS D233Q/E350Q          | ASLQIFNNIKDYNLDDNLLENPNNKFDDDEKYW | ITTVDTY | 876 |
| EndoS D233Q/D405A          | ASLQIFNNIKDYNLDDNLLENPNNKFDDDEKYW | ITTVDTY | 876 |
| EndoS D233Q/Y402F          | ASLQIFNNIKDYNLDDNLLENPNNKFDDDEKYW | ITTVDTY | 876 |

[Figure 4-7]

| Variant | 880 — 911 |
|---|---|
| EndoS D233Q | SAQGERATAFSNTLNNIHTSKKYWRVVFDDTKGDRYSS 911 |
| EndoS D233Q/Q303L | SAQGERATAFSNTLNNIHTSKKYWRVVFDDTKGDRYSS 911 |
| EndoS D233Q/Q303L/E350Q | SAQGERATAFSNTLNNIHTSKKYWRVVFDDTKGDRYSS 911 |
| EndoS D233Q/Q303L/D405A | SAQGERATAFSNTLNNIHTSKKYWRVVFDDTKGDRYSS 911 |
| EndoS D233Q/E350Q | SAQGERATAFSNTLNNIHTSKKYWRVVFDDTKGDRYSS 911 |
| EndoS D233Q/D405A | SAQGERATAFSNTLNNIHTSKKYWRVVFDDTKGDRYSS 911 |
| EndoS D233Q/Y402F | SAQGERATAFSNTLNNIHTSKKYWRVVFDDTKGDRYSS 911 |

| Variant | 912 — 946 |
|---|---|
| EndoS D233Q | PVVPELLQILLGYPLPNADTHIMKTVTTTAKELSQQKDK 946 |
| EndoS D233Q/Q303L | PVVPELLQILLGYPLPNADTHIMKTVTTTAKELSQQKDK 946 |
| EndoS D233Q/Q303L/E350Q | PVVPELLQILLGYPLPNADTHIMKTVTTTAKELSQQKDK 946 |
| EndoS D233Q/Q303L/D405A | PVVPELLQILLGYPLPNADTHIMKTVTTTAKELSQQKDK 946 |
| EndoS D233Q/E350Q | PVVPELLQILLGYPLPNADTHIMKTVTTTAKELSQQKDK 946 |
| EndoS D233Q/D405A | PVVPELLQILLGYPLPNADTHIMKTVTTTAKELSQQKDK 946 |
| EndoS D233Q/Y402F | PVVPELLQILLGYPLPNADTHIMKTVTTTAKELSQQKDK 946 |

| Variant | 947 — 981 |
|---|---|
| EndoS D233Q | FSQKMLDELKKIKEMALEETSLNSKIFDVTAINANAG 981 |
| EndoS D233Q/Q303L | FSQKMLDELKKIKEMALEETSLNSKIFDVTAINANAG 981 |
| EndoS D233Q/Q303L/E350Q | FSQKMLDELKKIKEMALEETSLNSKIFDVTAINANAG 981 |
| EndoS D233Q/Q303L/D405A | FSQKMLDELKKIKEMALEETSLNSKIFDVTAINANAG 981 |
| EndoS D233Q/E350Q | FSQKMLDELKKIKEMALEETSLNSKIFDVTAINANAG 981 |
| EndoS D233Q/D405A | FSQKMLDELKKIKEMALEETSLNSKIFDVTAINANAG 981 |
| EndoS D233Q/Y402F | FSQKMLDELKKIKEMALEETSLNSKIFDVTAINANAG 981 |

| Variant | 982 — 995 | SEQ ID |
|---|---|---|
| EndoS D233Q | VLKDCIEKRQLLKK 995 | SEQ ID NO:1 |
| EndoS D233Q/Q303L | VLKDCIEKRQLLKK 995 | SEQ ID NO:4 |
| EndoS D233Q/Q303L/E350Q | VLKDCIEKRQLLKK 995 | SEQ ID NO:5 |
| EndoS D233Q/Q303L/D405A | VLKDCIEKRQLLKK 995 | SEQ ID NO:6 |
| EndoS D233Q/E350Q | VLKDCIEKRQLLKK 995 | SEQ ID NO:7 |
| EndoS D233Q/D405A | VLKDCIEKRQLLKK 995 | SEQ ID NO:8 |
| EndoS D233Q/Y402F | VLKDCIEKRQLLKK 995 | SEQ ID NO:9 |

[High-mannose type]
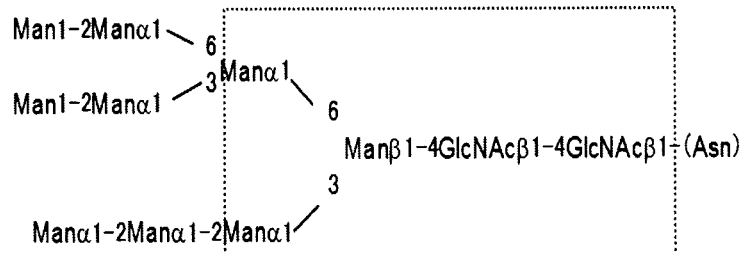
[Hybrid type]
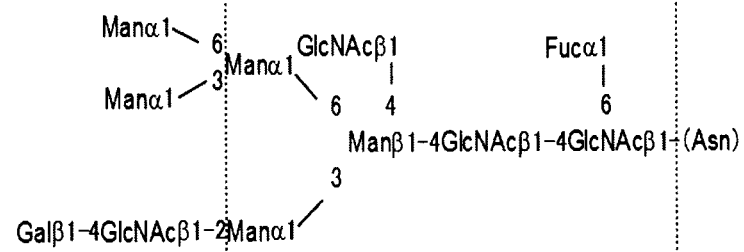
[Complex type]
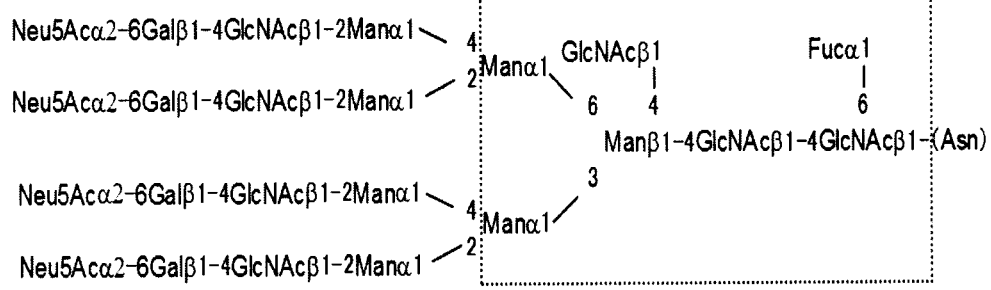
[Figure 5]

ENDOS MUTANT ENZYME

STATEMENT REGARDING SEQUENCE LISTING

The sequence listing associated with this application is provided in text format in lieu of a paper copy and is hereby incorporated by reference into the specification. The name of the text file containing the sequence listing is 65131 Sequence Listing ST25.txt. The text file is 22.3 KB; was created on Nov. 18, 2017; and is being submitted via EFS-Web.

TECHNICAL FIELD

The present invention relates to a novel mutant of endo-β-N-acetylglucosaminidase S (EndoS), a gene encoding the mutant, a recombinant plasmid, a transformant transformed with the plasmid, and a method for modifying a sugar chain of an antibody using the mutant.

BACKGROUND ART

Glycoproteins widely reside in tissue in animals and plants, the cell membrane and wall of eucaryotic microorganisms, and the like. Recently, it has been becoming clear that sugar chains of glycoproteins play important roles in mechanisms such as differentiation of cells, canceration, and cell-cell recognition and studies are underway on the correlation between the structure and the function of sugar chains to elucidate these mechanisms. In culture cell lines, a glycoprotein is translated as a protein consisting of a uniform amino acid sequence and then glycosylated by posttranslational modification to be delivered into the culture medium. Since this posttranslational modification is not determined uniquely according to its amino acid sequence, sugar chains that are added vary in their structures even on the same protein expressed in the same culture system.

Antibodies are glycoprotein molecules having N-linked sugar chains (N297-linked sugar chains) linked to the Asn side chains at position 297 located in the Fc regions of the heavy chain molecules. Antibodies are important molecules in basic studies and in the field of medicine and are eagerly studied and developed particularly as antibody medicines. As such, various effects of sugar chains are becoming clear (Non Patent Literature 1: J. N. Arnold, et al., Annu. Rev. Immunol, 2007, 25, 21050). Currently, the therapeutic antibodies that are used are mainly of the IgG class of molecules. Such antibodies are produced by cultured animal cells such as by CHO cells and NS0 cells in general and N297-linked sugar chains of antibodies produced by these animal cells are biantennary complex-type sugar chains, which are heterogeneous in the core fucose, the terminal sialyl and galactosyl groups, and bisecting GlcNAc (Non Patent Literature 2: R. Jefferis, Biotechnol. Prog., 2005, 21-11-6). It has been revealed that N297-linked sugar chains of antibodies have a large influence on effector activities including ADCC (antibody-dependent cell-mediated cytotoxicity) and CDC (Non Patent Literature 3: Nimmerjahn, Nat. Rev. Immunol. 2008, 8, 34-47; Non Patent Literature 4: Jefferis Nat. Rev. Drug Discovery, 2009, 8, 226-234) and the possibility that they also have an influence on half-life in blood has been reported (Non Patent Literature 5: D. Bumbaca, AAPSJ, 2012, 14, 3). Moreover, it has been revealed that antibodies 2,6-sialylated at the nonreducing terminals of the N297-linked sugar chains are active pharmaceutical ingredients in the IVIG (Non Patent Literature 6: Wang, ACS Chem. Biol. 2012, 7, 110-122). Moreover, it is considered that the heterogeneity of N297-linked sugar chains in therapeutic molecules including IgG and Fc fragments has a large influence on their nature and quality as an active ingredient and there is an undeniable possibility that contamination with a small amount of heterogeneously glycosylated molecules significantly changes the properties of end-products.

In response to this current situation, techniques for making sugar chains homogenous in the production of glycoprotein molecules including therapeutic antibodies and antibody Fc regions are being developed. Known methods for making sugar chains to be added to a glycoprotein homogenous include the transglycosidation reaction using enzymes (Non Patent Literature 6: Wang, ACS Chem. Biol. 2012, 7, 110-122; Non Patent Literature 7: Wang, Trends Glycosci. Glycotechnol. 2011, 23, 33-52). This is a multi-stage process consisting of cleavage (hydrolysis reaction) of sugar chains and condensation of sugar chains (transglycosylation reaction) in an in vitro environment. In particular, for the purpose of converting N-type sugar chains, a group of enzymes referred to as endo-β-N-acetylglucosaminidases are used. Such enzymes are required 1) to have an ability to hydrolyze complex-type sugar chains specifically as their substrates and 2) to have an ability to catalyze the transglycosylation reaction of a particular structure, as their properties. Endo-β-N-acetylglucosaminidases are isolated from various species and different wild type and mutant enzymes are used depending on the kind of sugar chains to be modified as substrates. EndoA (enzyme derived from *Arthrobacter protophormiae*) (Non Patent Literature 8: Takegawa, Biochem Int. 1991 July; 24(5): 849-55), EndoD (enzyme derived from *Streptococcus pneumoniae*) (Non Patent Literature 9: Fan, J Biol Chem. 2012 Mar 30; 287(14): 11272-81), EndoM (enzyme derived from *Mucor hiemalis*) (Non Patent Literature 10: Umekawa, Biochem Biophys Res Commun. 1994 Aug 30, 203(1): 244-52), EndoH (Non Patent Literature 11: Robbins, J Biol Chem. 1984 Jun 25; 259(12): 7577-83), EndoF2 (enzyme derived from *Flavobacterium Meningosepticum*) (Non Patent Literature 12: Huang, Chembiochem. 2011 April 11; 12(6): 932-941), EndoE (enzyme derived from *Enterococcus faecalis*) (Non Patent Literature 13: Collin, JBC 2004, 279-21), EndoS (enzyme derived from *Streptococcus pyogenes*) (Non Patent Literature 14: Collin, EMBO J. 2001 Jun 15; 20(12): 3046-55), and the like are used for the purpose of making sugar chains homogenous, but only EndoS is confirmed to be an enzyme having both hydrolysis activity and transglycosylation activity on a substrate which is complex-type N297-linked sugar chains having core fucose (Non Patent Literature 15: Allhorn, BMC Microbiol. 2008, 8, 3; Non Patent Literature 16: Goodfellow, J. Am. Chem. Soc. 2012, 134, 8030-8033).

Further known concerning EndoS is that the hydrolysis activity of EndoS D233Q (in which there is a mutation that substitutes Asp at position 233, the nucleophilic catalytic residue among the 2 catalytic residues (which are Asp at position 233 and Glu at position 235) with Gln) is suppressed to some extent. This mutant is known to catalyze the transglycosylation reaction selectively under conditions in which the reaction system contains a lot of intermediates having sugar chains with oxazolinated reducing terminals (Non Patent Literature 17: Huang, J. Am. Chem. Soc. 2012, 134, 12308-12318; Patent Literature 1: WO 2013/120066 A1; Non Patent Literature 18: B. Trastoy et al., PNAS (2014) vol 111, No. 18, pp6714-6719). Moreover, many sequences of enzymes classified as being EndoS enzymes that are sequences derived from different serotypes of different strains in the species pyogenes have been reported. In particular, EndoS2 derived from the serotype M49 (Non Patent Literature 19: Sjogren, Biochem J. 2013 Oct 1; 455(1): 107-18; which may also be referred to as EndoS49) has been reported to have similar substrate properties.

However, the activity of these known EndoS enzymes and mutant enzymes such as EndoS D233Q is not sufficient to perform sugar remodeling of therapeutic antibodies on an industrial scale and a technical improvement that makes effective sugar remodeling possible is required.

CITATION LIST

Patent Literature

Patent Literature 1: WO 2013/120066 A1 pamphlet

Non Patent Literature

Non Patent Literature 1: J. N. Arnold et al., Annu. Rev. Immunol, 2007, 25, 21050
Non Patent Literature 2: R. Jefferis, Biotechnol. Prog., 2005, 21-11-6
Non Patent Literature 3: Nimmerjahn, Nat. Rev. Immunol. 2008, 8, 34-47
Non Patent Literature 4: Jefferis Nat. Rev. Drug Discovery 2009, 8, 226-234
Non Patent Literature 5: D. Bumbaca, AAPSJ, 2012, 14, 3
Non Patent Literature 6: Wang, ACS Chem. Biol. 2012, 7, 110-122
Non Patent Literature 7: Wang, Trends Glycosci. Glycotechnol. 2011, 23, 33-52
Non Patent Literature 8: Takegawa, Biochem Int. 1991 July; 24(5): 849-55
Non Patent Literature 9: Fan, J Biol Chem. 2012 Mar. 30; 287(14): 11272-81
Non Patent Literature 10: Umekawa, Biochem Biophys Res Commun. 1994 Aug. 30; 203(1): 244-52
Non Patent Literature 11: Robbins, J Biol Chem. 1984 Jun. 25; 259(12): 7577-83
Non Patent Literature 12: Huang, Chembiochem. 2011 Apr. 11; 12(6): 932-941
Non Patent Literature 13: Collin, JBC 2004, 279-21
Non Patent Literature 14: Collin, EMBO J. 2001 Jun. 15; 20(12): 3046-55
Non Patent Literature 15: Allhorn, BMC Microbiol. 2008, 8, 3.;
Non Patent Literature 16: Goodfellow, J. Am. Chem. Soc. 2012, 134, 8030-8033
Non Patent Literature 17: Huang, J. Am. Chem. Soc. 2012, 134, 12308-12318
Non Patent Literature 18: B. Trastoy et al., PNAS (2014) vol 111, No. 18, pp6714-6719
Non Patent Literature 19: Sjogren, Biochem J. 2013 Oct. 1; 455(1): 107-18

SUMMARY OF INVENTION

Technical Problem

An object of the present invention is to provide a novel mutant enzyme having reduced hydrolysis activity in comparison with EndoS D233Q (which is known to be a mutant of endo-β-N-acetylglucosaminidase having specificity to sugar chains of the Fc regions of IgG and having suppressed hydrolysis activity in comparison with EndoS) and maintaining a certain transglycosylation activity.

From a study using the known EndoS D233Q, it was found that since this mutant maintains a certain hydrolysis activity, its transglycosylation rate in the transglycosylation reaction decreases over time after the onset of the reaction. Therefore, it is difficult to acquire an antibody having homogenous sugar chains at high purity by sugar remodeling with EndoS or existing mutants. In particular, in reactions at a large scale, a final-stage antibody separated from the enzyme inevitably contains the antibody with truncated sugar chains since the purification step takes a long time.

Furthermore, chemically synthesized oxazoline derivatives of sugar chains used as sugar donors are often expensive and their use in a large quantity leads to an increase in the production cost. Therefore, an enzyme having a reduced hydrolysis activity in comparison with EndoS D233Q and a transglycosylation activity equal to or higher than a certain level is necessary to produce an antibody having homogenous sugar chains at high purity.

Solution to Problem

As a result of diligent studies to achieve the aforementioned object, the present inventors have designed and produced a large number of mutants with reference to the amino acid sequence information and the 3D structure of EndoS D233Q and found that novel mutant enzymes having an additional mutation(s) of a particular amino acid(s) in addition to D233Q have the desired activity and further studies have been made to complete the present invention.

The present invention provides the following inventions:
(1) An EndoS mutant enzyme comprising an amino acid sequence of amino acid numbers 37 to 995 of SEQ ID NO: 2 with an additional mutation at at least one amino acid position selected from the group consisting of: amino acid 122 (H122), amino acid 184 (P184), amino acid 279 (D279), amino acid 282 (Y282), amino acid 303 (Q303), amino acid 348 (Y348), amino acid 350 (E350), amino acid 402 (Y402), amino acid 405 (D405), and amino acid 406 (R406), and exhibiting a reduced hydrolysis activity in comparison with the activity of EndoS D233Q, the activity being an activity on an N-linked sugar chain (N297-linked sugar chain) linked to Asn at position 297 in IgG.
(2) The EndoS mutant enzyme according to (1), wherein the additional mutation is at 1 to 4 amino acid positions selected from the group consisting of: H122, P184, D279, Y282, Q303, Y348, E350, Y402, D405, and R406.
(3) The EndoS mutant enzyme according to (1), wherein the additional mutation is a mutation at one amino acid position selected from the group consisting of: Q303, E350, and D405.
(4) The EndoS mutant enzyme according to any one of (1) to (3) (1) or (2), wherein the additional mutation is at least one selected from the following group:
a mutation at H122 to the amino acids: Gly, Cys, Thr, Ser, Val, Ala, Glu, Asp, Leu, Ile, Pro, Met, or Phe;
a mutation at P184 to the amino acids: Gly, Cys, Thr, Ser, Val, Pro, Ala, Gln, or Asn;
a mutation at D279 to the amino acids: Gly, Cys, Thr, Ser, Val, Pro, Ala, or Gln;
a mutation at Y282 to the amino acids: Arg, Lys, or His;
a mutation at Q303 to the amino acids: Met, Pro, or Leu;
a mutation at Y348 to the amino acids: His or Trp;

a mutation at E350 to the amino acids: Lys, Arg, His, Tyr, Gln, Asn, Asp, Gly, Cys, Thr, Ser, Val, Pro, or Ala;
a mutation at Y402 to the amino acids: Phe or Trp;
a mutation at D405 to the amino acids: Gly, Cys, Thr, Ser, Val, Pro, or Ala; and
a mutation at R406 to the amino acids: Gly, Cys, Thr, Ser, Val, Pro, Ala, Glu, Asp, Gln, or Asn.
(5) The EndoS mutant enzyme according to (4), wherein the additional mutation is at least one selected from the following group:
a mutation at H122 to Ala (H122A) or Phe (H122F);
a mutation at P184 to Gln (P184Q);
a mutation at D279 to Ser (D279S) or Gln (D279Q);
a mutation at Y282 to Arg (Y282R);
a mutation at Q303 to Leu (Q303L);
a mutation at Y348 to His (Y348H);
a mutation at E350 to Ala (E350A), Asn (E350N), Asp (E350D), or Gln (E350Q);
a mutation at Y402 to Phe (Y402F) or Trp (Y402W);
a mutation at D405 to Ala (D405A); and
a mutation at R406 to Gln (R406Q).
(6) The EndoS mutant enzyme according to (5), comprising at least one mutation selected from the group consisting of Q303L, E350A, E350N, E350D, E350Q, and D405A as the additional mutation.
(7) The EndoS mutant enzyme according to (6), wherein the additional mutation is Q303L, E350A, E350N, E350D, E350Q, D405A, H122A/Q303L, H122F/Q303L, P184Q/Q303L, D279Q/Q303L, D279S/Q303L, Y282R/Q303L, Q303L/Y348H, Q303L/E350A, Q303L/E350N, Q303L/E350D, Q303L/E350Q, Q303L/Y402F, Q303L/Y402W, Q303L/D405A, Q303L/R406Q, H122A/E350A, H122F/E350A, P184Q/E350A, D279Q/E350A, D279S/E350A, Y282R/E350A, Y348H/E350A, E350A/Y402F, E350A/Y402W, E350A/D405A, E350A/R406Q, H122A/E350N, H122F/E350N, P184Q/E350N, D279Q/E350N, D279S/E350N, Y282R/E350N, Y348H/E350N, E350N/Y402F, E350N/Y402W, E350N/D405A, E350N/R406Q, H122A/E350D, H122F/E350D, P184Q/E350D, D279Q/E350D, D279S/E350D, Y282R/E350D, Y348H/E350D, E350D/Y402F, E350D/Y402W, E350D/D405A, E350D/R406Q, H122A/E350Q, H122F/E350Q, P184Q/E350Q, D279Q/E350Q, D279S/E350Q, Y282R/E350Q, E350Q/Y348H, E350Q/Y402F, E350Q/Y402W, E350Q/D405A, E350Q/R406Q, H122A/D405A, H122F/D405A, P184Q/D405A, D279Q/D405A, D279S/D405A, Y282R/D405A, Y348H/D405A, or D405A/R406Q.
(8) The EndoS mutant enzyme according to (7), wherein the additional mutation is Q303L, E350A, E350N, E350D, E350Q, D405A, Q303L/E350A, Q303L/E350N, Q303L/E350D, Q303L/E350Q, Q303L/D405A, E350A/D405A, E350N/D405A, E350D/D405A, or E350Q/D405A.
(9) The EndoS mutant enzyme according to (4), wherein the additional mutation is H122A, H122F, P184Q, D279Q, D279S, Y282R, Y348H, Y402F, Y402W, or R406Q.
(10) The EndoS mutant enzyme according to (1), wherein the activity on the N297-linked sugar chain keeps a hydrolysis rate of 50% or less in a hydrolysis reaction in a reaction solution at pH 7.4 after 24 hours later.
(11) The EndoS mutant enzyme according to (1), wherein the EndoS mutant enzyme further exhibits an activity on the N297-linked sugar chain leading to a percent transglycosylation of approximately 60% or more after 48 hours of a transglycosylation reaction with 5 equivalents of a sugar donor relative to an acceptor molecule comprising the N297-linked sugar chain, in a reaction solution at pH 7.4.
(12) A polynucleotide encoding an EndoS mutant enzyme according to any one of (1) to (11).
(13) A vector comprising a nucleotide complementary to the polynucleotide according to (12).
(14) A host cell transformed with a vector according to (13).
(15) A method of production of a molecule comprising a sugar-remodeled Fc region, comprising reacting a molecule comprising an Fc region of IgG having a core GlcNAc optionally with fucose addition as an N297-linked sugar chain with a sugar donor having a structure comprising an oxazolinated GlcNAc in the presence of an EndoS mutant enzyme according to any one of (1) to (11) to produce a molecule comprising an Fc region with a N297-linked sugar chain having a structure in which a sugar chain possessed by the sugar donor is transferred to the core GlcNAc of the N297-linked sugar chain.
(16) The method of production according to (15), wherein the molecule comprising an Fc region is an IgG monoclonal antibody.

Advantageous Effects of Invention

The novel EndoS mutant enzymes of the present invention have a further reduced hydrolysis activity in comparison with EndoS D233Q, which is known to be a mutant having reduced hydrolysis activity, and maintain a transglycosylation activity equal to or higher than a certain level. Therefore an antibody having homogenous sugar chains can be acquired by sugar remodeling with the mutant enzymes of the present invention at a higher purity and more efficiently. Moreover, they lead to a decrease in the production cost of sugar-remodeled antibodies since the amount of sugar donor used in the sugar remodeling can be decreased.

BRIEF DESCRIPTION OF DRAWINGS

FIG. 1 illustrates a chemical structural formula (left) of SG-Oxa, which can be used as a sugar donor in sugar remodeling, and a representation (right) of the sugar chain in symbol form.

FIG. 2 is a schematic view of the hydrolysis reaction of an N297-linked sugar chain of an antibody using EndoS or an EndoS mutant enzyme.

FIG. 3 schematically illustrates the transglycosylation reaction using EndoS or an EndoS mutant enzyme.

FIG. 4 illustrates an alignment of the amino acid sequences of EndoS mutant enzymes (EndoS D233Q, EndoS D233Q/Q303L, EndoS D233Q/Q303L/E350Q, EndoS D233Q/Q303L/D405A, EndoS D233Q/E350Q, EndoS D233Q/D405A, and EndoS D233Q/Y402F). The amino acids are numbered based on the full length coding region including the signal sequence (1-36). FIG. 4-1 illustrates an alignment of amino acid numbers 37-176 of the mutant enzymes.

FIG. 4-2 is a continuation of FIG. 4-1 and illustrates an alignment of amino acid numbers 177-316 of the mutant enzymes.

FIG. 4-3 is a continuation of FIG. 4-2 and illustrates an alignment of amino acid numbers 317-456 of the mutant enzymes.

FIG. 4-4 is a continuation of FIG. 4-3 and illustrates an alignment of amino acid numbers 467-596 of the mutant enzymes.

FIG. 4-5 is a continuation of FIG. 4-4 and illustrates an alignment of amino acid numbers 597-736 of the mutant enzymes.

FIG. 4-6 is a continuation of FIG. 4-5 and illustrates an alignment of amino acid numbers 737-876 of the mutant enzymes.

FIG. 4-7 is a continuation of FIG. 4-6 and illustrates an alignment of amino acid numbers 877-995 of the mutant enzymes.

FIG. 5 illustrates types of human N-linked sugar chains.

DESCRIPTION OF EMBODIMENTS

The present invention is described in detail below.

The notation of amino acids contained in a molecule herein conforms to the customs of the field and the position of a mutation is indicated by the one character notation of the wildtype amino acid (or nucleic acid) and its number (for example, Asp at position 233 is referred to as "D233"). Mutations are indicated by the one character notation of the wildtype amino acid (or nucleic acid), its number, and the one character notation of the amino acid (or nucleic acid) after the mutation (for example, the mutation that substitutes Asp at position 233 with Gln is referred to as "D233Q"). Moreover, particular mutants having a mutation are indicated by the molecule name and the mutation (for example, the mutant of EndoS in which Asp at position 233 is substituted with Gln is referred to as "EndoS D233Q") and, if the mutant has a plurality of mutations, the mutations are indicated with a separator "/" between the mutations (for example, the mutant of EndoS D233Q having an additional mutation that substitutes Gln at position 303 with Leu is referred to as "EndoS D233Q/Q303L").

In the present invention, the term "N297-linked sugar chains" means sugar chains linked to the Asn side chain at position 297 of an IgG heavy chain. When an IgG is fragmented, a sugar chain linked to the corresponding Asn in a peptide fragment containing the Asn is also included within the term "N297-linked sugar chain". Usually, the N297-linked sugar chains in IgG produced in animals and the like have a basic structure represented by the following formula and Gal or sialic acid may be further added to their nonreducing terminals.

Most N297-linked sugar chains of IgG produced by cells have a variety of sugar chain structures, including sugar chains in which further sugar chains are linked to a GlcNAc at the reducing terminal(core GlcNAc) and/or moiety at the nonreducing terminals, branched sugars, or the like in this basic structure. The core GlcNAc may be modified into the structure ((Fucα1,6)GlcNAc) having a core fucose in which fucose is α1,6 linked to the 6th position of the core GlcNAc. The branched mannose may form a tribranched type sugar chain in which a further sugar chain containing GlcNAc is linked to the 5th position of mannose. To GlcNAc at the nonreducing terminals, sugar chains containing Gal or sialic acid may be linked.

In the present invention, "sugar donors" are sugar chain-containing molecules having oxazolinated GlcNAc at the reducing terminals of their sugar chains and molecules with various sugar chain structures are available.

When sugar donors are used for sugar remodeling for the purpose of drug discovery, it is preferred to employ a sugar donor having a human sugar chain or a human-compatible sugar chain that causes few problems when applied to humans. Such sugar chains are sugar chains known to exhibit no antigenicity in the human body and known examples of such sugar chains that are N-linked sugar chains include the high-mannose type, the hybrid type, and the complex type. These 3 have common basic structures. The high-mannose type of sugar chains are those having a mannose-rich structure in which a plurality of mannose residues are connected to the 2 branched chains (the 1-3 and 1-6 chains) branched from mannose (Δ-mannose) at the position close to the reducing terminal. The hybrid type of sugar chains are those in a structure having GlcNAc in one of the 2 branched chains (the 1-3 and 1-6 chains) branched from mannose (13-mannose) at the position close to the reducing terminal. The complex type of sugar chains are those that are in a structure having GlcNAc in the 2 branched

[Formula 1]

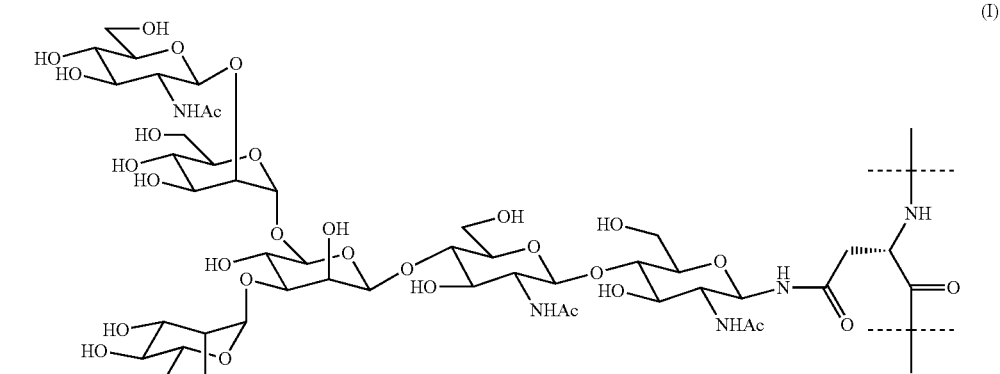

(I)

[Formula 2]

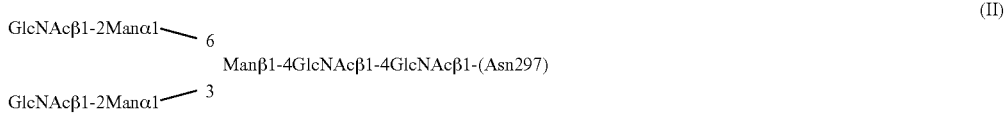

(II)

chains (the 1-3 and 1-6 chains) branched from mannose (Δ-mannose) at the position close to the reducing terminal and have various structures including those with or without galactose, with or without sial, and linkage isomers and regioisomers thereof. (See FIG. 5).

Types of human N-linked sugar chains are shown in FIG. 5.

In the present invention, "acceptor molecules" are molecules containing a sugar structure having GlcNAc at a nonreducing terminal and, when they are reacted with sugar donor molecules in the presence of EndoS or a mutant enzyme thereof, they can form the chitobiose structure as a result of the reaction of the oxazoline rings in the sugar donor molecules with the 4th position of GlcNAc at a nonreducing terminal of the acceptor molecules. A typical acceptor molecule is IgG or an Fc fragment thereof that is derived from a monoclonal antibody and has an N297-linked sugar chain only consisting of core GlcNAc optionally linked with core fucose. To the core GlcNAc, core fucose may or may not be linked depending on the antibody from which the acceptor molecule is derived or the method of production thereof. Various monoclonal antibodies or molecules comprising an Fc region (such as Fc, CLCH, which is a combination of CH, only, consisting of the constant region obtained by deleting the variable region from the heavy chain and CL, only, consisting of the constant region of the light chain) may be used as a source of acceptor molecules, but preferable examples thereof include (Fucα1,6)-GlcNAc-IgG, (Fucα1,6)-GlcNAc-Fc, and (Fucα1,6)-GlcNAc-CLCH and representative examples include (Fucα1,6)-GlcNAc-Trastuzumab, which is produced in Example 3.

In the present invention, "EndoS" is a kind of endo-β-N-acetylglucosaminidase (ENGase) derived from Streptococcus pyogenes and the enzyme consists of an amino acid sequence of amino acid numbers 37 to 995 (amino acids at positions 1 to 36 correspond to a signal sequence) of SEQ ID NO: 1 in which the amino acid at position 233 is Asp (EC 3.2.1.96, GH18). EndoS specifically recognizes N297-linked sugar chains on the Fc site of IgG and has both hydrolysis activity and transglycosylation activity. The hydrolysis activity of EndoS is the activity that specifically hydrolyzes the β-1,4-glycosidic bond contained in the core chitobiose of N297-linked sugar chains having the basic structure described above (as used herein, unless otherwise specified, "hydrolysis activity" means this activity; a schematic view of the reaction is shown in FIG. 2). The transglycosylation activity of EndoS is the activity that forms a glycosidic bond between the reducing terminal of a sugar chain derived from a sugar donor having oxazolinated GlcNAc (core fucose may or may not be added) at the reducing terminal and an acceptor molecule containing an Fc site having only core GlcNAc at N297 (this activity is, hereinafter, referred to as "transglycosylation activity"; a schematic view of the reaction is shown in FIG. 3).

The structure of EndoS has been reported to be a 5 domain structure: the endoglycosidase enzymatic domain (catalytic domain: amino acid numbers 98 to 445 of SEQ ID NO: 1), the leucine-rich repeat domain (amino acid numbers 446 to 631 of SEQ ID NO: 1), the hybrid Ig domain (amino acid numbers 632 to 764 of SEQ ID NO: 1), the carbohydrate-binding module (CBM: amino acid numbers 765 to 923 of SEQ ID NO: 1), and the three helix-bundle domain (amino acid numbers 924 to 995 of SEQ ID NO: 1) (B. Trastoy et al., PNAS (2014) vol 111, No. 18, pp6714-6719), among which the sites that are important to the interaction with antibodies are considered to be the following two domains: the catalytic domain and CBM.

EndoS is an enzyme well conserved in Group A Streptococcus (GAS). EndoS2 (which may also be referred to as EndoS49; Sjogren, Biochem J. 2013 Oct. 1; 455(1): 107-18; US 2014/0302519 A1) found in NZ131 belonging to the serotype M49 of GAS has a sequence identity of 37%, but the important amino acids composing the catalytic domain are well conserved and EndoS2 exhibits a substrate specificity similar to EndoS. As used herein, such enzymes having an amino acid homology/identity with the active region of EndoS are referred to as "EndoS-related enzymes". The important mutation positions, H122, D233, D279, Q303, E350, Y402, D405, and R406 in EndoS respectively correspond to H75, D184, D226, Q250, E289, Y339, D342, and R343 in EndoS2. The mutant enzymes of the present invention also include mutant enzymes in which corresponding amino acids are mutated from related enzymes such as EndoS2.

In the present invention, "EndoS D233Q" is a mutant enzyme consisting of a sequence in which Asp at position 233 in wild type EndoS is substituted with Gln (the amino acid sequence of amino acid numbers 37 to 995 of SEQ ID NO: 1) and the mutant enzyme has the hydrolysis activity of EndoS suppressed by a certain degree and maintains the transglycosylation activity at the level equivalent to the wild type.

<Mutant Enzyme of the Present Invention>

The present invention provides EndoS D233Q mutant enzymes that contain the region necessary for the transglycosylation activity in the amino acid sequence of amino acid numbers 37 to 995 of SEQ ID NO: 2 and that have an additional mutation at at least one amino acid position selected from the group of positions of certain essential additional mutations, in addition to D233Q; and that have reduced hydrolysis activity to N297-linked sugar chains of IgG in comparison with EndoS D233Q.

In the present invention, the term "additional mutations" means additional amino acid alterations of amino acids other than D233 in the amino acid sequence of EndoS D233Q. In the present invention, the "group of positions of essential additional mutations" is a candidate group of positions that are necessarily mutated additionally in the mutant enzymes of the present invention and is the group consisting of the positions indicated by Xaa in the amino acid sequence of SEQ ID NO: 2, that is to say, H122, P184, D279, Y282, Q303, Y348, E350, Y402, D405, and R406, and is preferably the group consisting of Q303, E350, and D405.

The mutant enzymes of the present invention are characterized by having both hydrolysis activity lower than EndoS D233Q and a certain level of transglycosylation activity (hereinafter, having both activities is referred to as having "the present enzyme activity"). As to whether a mutant enzyme has the present enzyme activity, the hydrolysis and transglycosylation activities can be evaluated by a method of Example 4 described below.

As regards the present enzyme activity that the mutant enzymes of the present invention have, the hydrolysis activity is suppressed in comparison with hydrolysis activity of EndoS D233Q and, more specifically, the percent hydrolysis in conditions at pH 7.4 as described in Example 4 exhibits a value lower than the percent hydrolysis of EndoS D233Q at any one time point from the onset of the reaction to 1 to 48 hours later, but preferably the percent hydrolysis at 24 hours after the onset of the hydrolysis reaction is 50% or less or the percent hydrolysis at 48 hours later is 60% or less than that of EndoS D233Q, more preferably the percent hydrolysis is maintained at 40% or less than that of EndoS D233Q for 24 hours from the onset of the hydrolysis reaction, further preferably at 30% or less, even more preferably at 20% or less for the same time period, and most preferably the percent hydrolysis exhibited is 0% at all time points and the hydrolysis activity is diminished completely.

As regards the present enzyme activity that the mutant enzymes of the present invention have, the transglycosylation activity is at a level equivalent to the transglycosylation activity of EndoS D233Q and, more specifically, the percent transglycosylation in conditions at pH 7.4 with 5 equivalents of a sugar donor relative to an acceptor molecule comprising the N297-linked sugar chain as described in Example 4 is equal to or more than the percent transglycosylation of EndoS D233Q (for example, 70% or more of the value of EndoS D233Q) at and after a time point of 1 to 48 hours after the onset of the reaction, but preferably the percent transglycosylation achieves 50% or more than that of EndoS D233Q by 48 hours after the onset of the reaction, more preferably the percent transglycosylation achieves 60% or more than that of EndoS D233Q by 48 hours after the onset of the reaction, further preferably the percent transglycosylation achieves 80% or more than that of EndoS D233Q by 48 hours after the onset of the reaction, and even more preferably the percent transglycosylation achieves 90% or more than that of EndoS D233Q by 48 hours after the onset of the reaction.

The mutant enzymes of the present invention do not have to be of the full length sequence as long as the regions important for the transglycosylation activity of EndoS D233Q are conserved in the amino acid sequence of amino acid numbers 37 to 995 of SEQ ID NO: 2. From domain analyses of EndoS, it is known that the catalytic domain (amino acid numbers 98 to 445 of SEQ ID NO: 2) and CRM (amino acid numbers 765 to 923 of SEQ ID NO: 2) are important and mutant enzymes can be used as the mutant enzymes of the present invention, as long as they contain these domains. In addition, the present invention also includes related enzymes such as EndoS2 as long as they contain regions corresponding to these domain regions and have mutations of amino acids at corresponding positions (H122, D233, D279, Q303, E350, Y402, D405, and R406 of EndoS respectively correspond to H75, D184, D226, Q250, E289, Y339, D342, and R343 of EndoS2) as appropriate and display the present enzyme activity. They are preferably polypeptides containing amino acid numbers 98 to 923 of SEQ ID NO: 2, more preferably polypeptides containing amino acid numbers 98 to 995 of SEQ ID NO: 2, and further preferably polypeptides containing amino acid numbers 37 to 995 of SEQ ID NO: 2.

In the amino acid sequences of the mutant enzymes of the present invention, one to several amino acids may be substituted, deleted, inserted, and/or added at positions other than the positions of essential mutations described below to the extent that it does not affect the present enzyme activity. Any positions may be selected for such amino acid alterations as long as it does not affect the present enzyme activity, but the position is preferably a position out of the catalytic domain (amino acid numbers 98 to 445 of SEQ ID NO: 2) and CRM (amino acid numbers 765 to 923 of SEQ ID NO: 2) and more preferably a position contained in the regions of amino acid numbers 37 to 97 or amino acid numbers 924 to 995 of SEQ ID NO: 2. In the present invention, the term "several" refers to 20 or less, preferably 10 or less, further preferably 5 or less, and most preferably 4, 3, 2, or 1.

In a mutant enzyme of the present invention, the positions for additional mutations other than D233Q include at least one of the positions selected from the group of the positions of the essential additional mutations. The number of positions for additional mutations is not particularly limited as long as the produced mutant enzyme has the present enzyme activity, but it is preferably 10 or less, more preferably 5 or less, and further preferably 4, 3, 2, or 1. When the mutant enzyme has additional mutations at plural positions, if there is a mutation at at least one of the group of positions of essential additional mutations, then the other positions of mutation are not particularly limited as long as the produced mutant enzyme has the present enzyme activity, but it is preferred that all additional mutations are in the group of positions of essential additional mutations. When the mutant enzyme has an additional mutation at a position other than the positions of essential additional mutations, the region containing the additional mutation at a position other than the positions of essential additional mutations is preferably of an amino acid outside of the catalytic domain (amino acid numbers 98 to 445 of SEQ ID NO: 2), which relates to the enzyme activity, more preferably the region of amino acid numbers 37 to 97, 446 to 764, and 924 to 995 of SEQ ID NO: 2, and further preferably the region of amino acid numbers 37 to 97 and 924 to 995 of SEQ ID NO: 2.

In the present invention, the amino acid after performing the substitution of the additional mutation is not particularly limited as long as the finally obtained mutant enzyme has the present enzyme activity and any of various amino acids such as naturally occurring amino acids, artificially synthesized amino acids, and modified amino acids thereof may be used, but the amino acid is preferably a naturally occurring amino acid, more preferably a naturally occurring L-amino acid, and further preferably an essential amino acid. Amino acids that are preferred for the mutant amino acid at one of the positions of essential additional mutations are illustrated below.

The mutant amino acid at H122 is preferably an amino acid (Gly, Cys, Thr, Ser, Val, Pro, Ala) having a small side chain structure, such as those that diminish the interaction between the position and the surrounding amino acids, an amino acid (Glu or Asp) having a minus charge in the side chain, or an amino acid (Leu, Ile, Pro, Met, Phe) that has no highly reactive functional group in the side chain and more preferably Ala or Phe.

The mutant amino acid at P184 is preferably an amino acid (Gly, Cys, Thr, Ser, Val, Pro, Ala) having a small side chain structure or an amino acid (Gln, Asn) that has an amide group in the side chain and more preferably Gln.

The mutant amino acid at D279 is preferably an amino acid (Gly, Cys, Thr, Ser, Val, Pro, Ala) having a small side chain structure or Gln and more preferably Ser or Gln.

The mutant amino acid at Y282 is preferably an amino acid (Arg, Lys, His) whose side chain is basic and more preferably Arg.

The mutant amino acid at Q303 is preferably a hydrophobic amino acid (Met, Pro, Leu) and more preferably Leu.

The mutant amino acid at Y348 is preferably an amino acid (His, Trp) having a ring structure in the side chain and more preferably His.

The mutant amino acid at E350 is preferably an amino acid (Lys, Arg, His, Tyr, Gln, Asn) having a large side chain capable of forming a hydrogen bond or an amino acid (Gly, Cys, Thr, Ser, Val, Pro, Ala) having a small side chain structure, such as those that diminish the interaction between the position and the surrounding amino acids, and more preferably Ala, Asn, Asp, or Gln.

The mutant amino acid at Y402 is preferably a large amino acid having an aromatic ring in the side chain, Phe or Trp.

The mutant amino acid at D405 is preferably an amino acid (Gly, Cys, Thr, Ser, Val, Pro, Ala) having a small side chain structure, such as those that diminish the interaction between the position and the surrounding amino acids and more preferably Ala.

The mutant amino acid at R406 is preferably an amino acid (Gly, Cys, Thr, Ser, Val, Pro, Ala) having a small side chain structure, such as those that diminish the interaction between the position and the surrounding amino acids, or an amino acid (Glu, Asp) having a minus charge in the side chain, or an amino acid (Gln, Asn) that has an amide group in the side chain and more preferably Ala or Gln.

The mutation at the position of an essential additional mutation as described above may be alone or combined with a mutation at the position of another essential additional mutation and/or a mutation at another position. The combination of mutations at positions of essential additional mutations may be any combination, but is preferably a combination containing a mutation at at least Q303, E350, or D405 and more preferably a combination containing at least Q303L, E350A, E350N, E350Q, or D405A.

Examples of the combination of additional mutations containing Q303L can include H122A/Q303L, H122F/Q303L, P184Q/Q303L, D279Q/Q303L, D279S/Q303L, Y282R/Q303L, Q303L/Y348H, Q303L/E350A, Q303L/E350N, Q303L/E350D, Q303L/E350Q, Q303L/Y402F, Q303L/Y402W, Q303L/D405A, and Q303L/R406Q.

Examples of the combination of additional mutations containing E350A can include H122A/E350A, H122F/E350A, P184Q/E350A, D279Q/E350A, D279S/E350A, Y282R/E350A, Y348H/E350A, E350A/Y402F, E350A/Y402W, E350A/D405A, and E350A/R406Q.

Examples of the combination of additional mutations containing E350N can include H122A/E350N, H122F/E350N, P184Q/E350N, D279Q/E350N, D279S/E350N, Y282R/E350N, Y348H/E350N, E350N/Y402F, E350N/Y402W, E350N/D405A, and E350N/R406Q.

Examples of the combination of additional mutations containing E350D can include H122A/E350D, H122F/E350D, P184Q/E350D, D279Q/E350D, D279S/E350D, Y282R/E350D, Y348H/E350D, E350D/Y402F, E350D/Y402W, E350D/D405A, and E350D/R406Q.

Examples of the combination of additional mutations containing E350Q can include H122A/E350Q, H122F/E350Q, P184Q/E350Q, D279Q/E350Q, D279S/E350Q, Y282R/E350Q, Y348H/E350Q, E350Q/Y402F, E350Q/Y402W, E350Q/D405A, and E350Q/R406Q.

Examples of the combination of additional mutations containing D405A can include H122A/D405A, H122F/D405A, P184Q/D405A, D279Q/D405A, D279S/D405A, Y282R/D405A, Y348H/D405A, Y402F/D405A, Y402W/D405A, or D405A/R406Q.

Preferred mutant enzymes of the present invention are EndoS D233Q/Q303L, EndoS D233Q/E350A, EndoS D233Q/E350N, EndoS D233Q/E350D, EndoS D233Q/E350Q, EndoS D233Q/D405A, EndoS D233Q/Q303L/E350A, EndoS D233Q/Q303L/E350N, EndoS D233Q/Q303L/E350D, EndoS D233Q/Q303L/E350Q, EndoS D233Q/Q303L/D405A, EndoS D233Q/E350A/D405A, EndoS D233Q/E350N/D405A, EndoS D233Q/E350D/D405A, EndoS D233Q/E350Q/D405A, or EndoS D233Q/Y402F, more preferably EndoS D233Q/Q303L, EndoS D233Q/Q303L/E350Q, EndoS D233Q/Q303L/D405A, EndoS D233Q/E350A, or EndoS D233Q/Y402F.

<Gene, Host Cell, Method of Producing Enzyme>

The present invention further provides a recombinant gene encoding a mutant enzyme having an additional mutation in EndoS D233Q as described above, a gene construct such as a plasmid or an expression vector comprising the recombinant gene, a host cell transformed with the gene construct, a method of producing the mutant enzyme of the present invention, comprising the step of collecting the mutant enzyme of the present invention from a culture of the host cell, and the like. The recombinant gene, gene construct, host cell, and the like can be made according to known genetic engineering techniques based on the amino acid sequences of the mutant enzymes of the present invention.

With regard to a recombinant gene encoding a mutant enzyme of the present invention, a polynucleotide such as a cDNA encoding an amino acid sequence containing an additional mutation of interest can be made based on the nucleotide sequence of EndoS D233Q set forth in nucleotide numbers 109 to 2985 (1 to 108 is the region encoding the signal peptide) of SEQ ID NO: 3. For example, the nucleotide sequence encoding EndoS D233Q/Q303L is a nucleotide sequence modified from the nucleotide sequence of nucleotide numbers 109 to 2985 of SEQ ID NO: 3 by substituting the nucleotides CAG at position 907 to 909 with CTG. Moreover, the nucleotide sequence encoding EndoS D233Q/E350A (N, Q) is a nucleotide sequence modified from the nucleotide sequence of nucleotide numbers 109 to 2985 of SEQ ID NO: 3 by substituting the nucleotides GAA at position 1048 to 1050 with GCA (AAT in E350N and CAG in E350Q). Moreover, the nucleotide sequence encoding EndoS D233Q/D405A is a nucleotide sequence modified from the nucleotide sequence of nucleotide numbers 109 to 2985 of SEQ ID NO: 3 by substituting the nucleotides GAT at position 1213 to 1215 with GCA.

Host cells (cells, such as animal cells, plant cells, *Escherichia coli*, yeast, or the like, usually used for protein production may be selected as appropriate) transformed by the introduction of a gene encoding a mutant enzyme of the present invention are cultured under appropriate conditions depending on the kind of cell and the mutant enzyme of the present invention can be collected from the culture. The collection of the mutant enzyme is performed by combining usual purification techniques based on the physical properties of the enzyme as appropriate. To facilitate the collection, the gene construct may be designed to express the mutant enzyme in a form with a tag peptide such as GST connected to the mutant enzyme in advance to make collection using affinity to the tag peptide possible. The tag peptide may be removed after purification, but, when it has no effect on the enzyme activity, a mutant enzyme with the tag peptide connected thereto may be used for reactions such as sugar remodeling. The mutant enzymes of the present invention include such enzymes having an amino acid sequence comprising that of a tag peptide connected thereto.

<Sugar Remodeling>

The present invention provides a method of sugar remodeling of an N297-linked sugar chain on IgG or a molecule comprising an Fc region using an EndoS mutant enzyme of the present invention and IgG or a molecule comprising an Fc region having an N297-linked sugar chain consisting of a substantially homogenous structure obtained by the sugar remodeling.

The term "sugar remodeling" means a method for producing IgG or a molecule comprising an Fc region having N297-linked sugar chains which have a homogenous sugar chain structure derived from a sugar donor by first producing acceptor molecules in which N297-linked sugar chains of the molecule comprising an Fc region, such as IgG or a Fc fragment or CLCH (which only consists of the constant region) of IgG of a particular monoclonal antibody, are cut off except for a core GlcNAc (a core fucose may be added thereto); and then transferring a sugar chain derived from a sugar donor onto the core GlcNAc of the acceptor molecule using the transglycosylation activity of an EndoS mutant enzyme of the present invention.

The IgG, or molecule comprising an Fc region used in sugar remodeling, may be one derived from an IgG heavy chain, wherein the amino acid sequence of the IgG heavy chain is the same as that of the original molecule and produced in a form having an N297-linked sugar chain and methods of production thereof are not limited, but IgG produced by a commonly known method of producing a monoclonal antibody, CLCH of the IgG, or an Fc fragment obtained by enzymatic treatment thereof may also be used. In addition, a mixture of samples obtained by different methods of production in different lots may be used as such IgG or Fc fragment.

A method for preparing an acceptor molecule to be used in sugar remodeling may comprise preparing the acceptor molecule by treating the IgG or molecule comprising an Fc region described above with an ENGase which maintains the activity of specifically hydrolyzing the 1,4-glycosidic bond between GlcNAc in the core chitobiose structure of the N297-linked sugar chain. In this case, as the ENGase, various enzymes including EndoA, EndoD, EndoE, and EndoS may be used, but the ENGase is preferably wild type EndoS.

As the sugar donor to be used in sugar remodeling, molecules having various sugar chain structures may be employed. However, for the purpose of using the antibody after remodeling as an antibody medicine, it is preferred to employ a sugar donor having a human sugar chain structure, which is similar to, or the same as, the sugar chain structure that humans have or a human-compatible sugar chain structure. Representative examples of such a sugar donor can include molecules having a structure modified from the aforementioned basic structure of N-linked sugar chains by removing the core GlcNAc and oxazolinating the second GlcNAc from the reducing terminal and the sugar donor is preferably SG-Oxa consisting of the structure illustrated in FIG. 1.

As the reaction conditions for the hydrolysis reaction in sugar remodeling, those in commonly known methods for EndoS may be employed. The reaction is performed in a buffer solution, which may be selected as appropriate from buffer solutions used in usual enzymatic reactions: such as a citrate buffer solution (pH 3.5-5.5), an acetate buffer solution (pH 4.5-6.0), a phosphate buffer solution (pH 6.0-7.5), a MOPS-NaOH buffer solution (pH 6.5-8.0), and a Tris-HCl buffer solution (pH 7.0-9.0). A preferred buffer solution is a Tris-HCl buffer solution (pH 7.0-9.0). To the reaction solution, an additive that does not inhibit the enzymatic reaction may be added for the purpose of stabilizing the enzyme, but it is not necessary.

The reaction temperature may be selected in the range from 10° C. to 50° C. as appropriate, but the preferable temperature is from 25° C. to 38° C.

The reaction time may be selected as appropriate in the range from 10 minutes to 96 hours, but the end of the reaction may be determined by collecting small quantities of the reaction solution over time and confirming the degree of progress of hydrolysis. In general, the degree of progress of the sugar chain hydrolysis reaction may be monitored by sodium dodecyl sulfate-polyacrylamide gel electrophoresis (SDS-PAGE), fully automatic electrophoretic systems, liquid chromatography-mass spectrometry (LC-MS), or the like. In this patent, a commercially available antibody or a sugar remodeled antibody was fragmented into heavy and light chains and then they were examined with a fully automatic electrophoretic system to confirm that only the heavy chain, to which N297-linked sugar chains were added, was changed in the retention time.

The reaction conditions for the transglycosylation in sugar remodeling may be selected as appropriate based on conditions known for other enzymes.

The reaction is performed in a buffer solution and such a buffer is preferably one that does not promote the degradation of SG-Oxa and may be selected from a phosphate buffer solution (pH 6.0-7.5), a MOPS-NaOH buffer solution (pH 6.5-8.0), and a Tris-HCl buffer solution (pH 7.0-9.0) as appropriate. A preferred buffer is a Tris-HCl buffer solution (pH 7.0-9.0). Into the reaction solution, an additive that does not inhibit the enzymatic reaction may be added for the purpose of stabilizing the enzyme, but it is not necessary.

The reaction temperature may be selected in the range from 10° C. to 50° C. as appropriate, but the preferable temperature is from 25° C. to 38° C.

The reaction time may be selected as appropriate in the range from 10 minutes to 96 hours, but the end of the reaction may be determined by collecting small quantities of the reaction solution over time and confirming the degree of progress of the transglycosylation reaction. In general, the degree of progress of transglycosylation reaction may be monitored by sodium dodecyl sulfate-polyacrylamide gel electrophoresis (SDS-PAGE), fully automatic electrophoretic systems, liquid chromatography-mass spectrometry (LC-MS), or the like. In this patent, a commercially available antibody or a sugar remodeled antibody was fragmented into heavy and light chains and then they were examined with a fully automatic electrophoretic system to confirm that only the heavy chain, to which N297-linked sugar chains were added, was changed in the retention time.

EXAMPLES

The present invention is specifically described referring to the Examples below. The description in the Examples is an example of embodiments of the present invention and the present invention is not limited thereto.

Example 1 is a preparation example of EndoS mutant enzymes used in the present invention. Example 2 is a production example of the sugar donor used in the present invention. Example 3 is a preparation example of the acceptor molecule used in measuring transglycosylation activity. Example 4 is a measurement example of the percent hydrolysis by the EndoS mutant enzymes of the present invention and a measurement example of the percent transglycosylation by the EndoS mutant enzymes of the present invention.

The protein concentrations described herein were quantified with an ultramicrospectrophotometer NanoDrop 1000 (a product made by Thermo Fisher Scientific) or NanoDrop 2000 (a product made by Thermo Fisher Scientific).

The mass of sugar remodeled antibodies ((Fucα1,6) GlcNAc-Trastuzumab and SG-Trastuzumab) was confirmed by the following method. The sugar remodeled antibodies were fragmented into heavy and light chains and then their peaks were separated with an analytical column and analyzed by mass spectrometry. Apparatuses used were ACUITY UPLC (a product made by Waters), SYNAPT G2-S (Waters), and BEH Phenyl column (1.7 μm, 1.0×50 mm), the mobile phase used was acetonitrile with 0.05% trifluoroacetic acid in a gradient changing from 25% to 35% in 3 minutes, and the analysis was conducted at a flow rate of 0.34 μL/min at 80° C.

Example 1

Preparation of Reaction Solution of EndoS Mutant Enzymes (1-1) Design of EndoS Mutant Enzymes EndoS mutants that were considered to achieve suppressed hydrolysis activity while maintaining the transglycosylation activity of EndoS D233Q by introducing a mutation(s) into EndoS D233Q were designed. Based on the 3D structure information (PDB ID:4NUY) of EndoS, the catalytic domain of EndoS was divided into 3 groups of sites: sites predicted to be involved in the recognition of sugar chains, sites in the vicinity of the active center, and sites predicted to be involved in the recognition of antibodies. Mutations were introduced to the sites. The 6 residues H122, Y348, E350, Y402, D405 and R406 were selected as the sites predicted to be involved in the recognition of sugar chains and enzymes were designed such that the interaction formed by the amino acid residues described above should be cut or such that amino acid residues having a large side chain among the selected amino acids should be substituted with amino acid residues having a small side chain in order to make turnover of coupling and dissociation of the sugar chain efficient. P184, D279, and Q303 were selected as sites in the vicinity of the active center and mutations were designed to substitute them with a wide variety of amino acids including those having properties similar to the wildtype amino acid residue or those having properties different from the wildtype amino acid residue. Y282 is selected as one of the sites predicted to be involved in the recognition of antibodies and a mutation was designed to substitute the amino acid residue with a basic amino acid in order to strengthen the interaction with the minus charge near Asn 297 to which sugar chains of antibodies link. The mutant enzymes set forth in Table 2 were designed in the 3 sites described above or in consideration of combined mutations among the 3 sites.

(1-2) Expression of EndoS Mutant Enzymes

*Escherichia coli* was transformed by adding 3 μL of a plasmid (pGEX4T3, 50 μg/μL) for protein expression containing a gene encoding the amino acid sequence of each of the EndoS mutant enzymes designed based on (1-1) above to 50 μL of ice-cooled *Escherichia coli* BL21 (DE3) strain having a competency of $10^7$ cfu/μL and heating the mixture at 37° C. for 40 seconds. These *Escherichia coli* cells were cultured overnight on LB agar medium containing 100 μg/mL of ampicillin and colonies obtained on the next day were picked up and cultured with shaking in 1 L of TB medium containing 100 μg/mL of ampicillin at 37° C. until O.D. 600 reached 0.8. After O.D. 600 increased, the culture temperature was lowered to 16° C. and 1 hour later isopropyl β-D-1-thiogalactopyranoside (IPTG) was added to a final concentration of 0.1 mM to induce the expression of the EndoS mutant enzyme overnight. On the next day, cells were collected by centrifuging the liquid culture at 5000×G for 10 minutes and 50 mL of PBS buffer with 40 U/mL DNase I and 0.5 mg/mL Lysozyme was added to resuspend the cells. The cells were disrupted by sonicating the obtained bacterial suspension and centrifuged at 20000×g for 30 minutes to obtain the target EndoS mutant enzyme in the soluble fraction.

(1-3) Purification of EndoS Mutant Enzymes

The soluble fractions of the EndoS mutant enzymes obtained in (1-2) above were filtrated through a PVDF membrane having a pore size of 0.45 μm and the solutions after the filtration were purified by the 2 steps process by glutathione affinity chromatography and gel filtration chromatography.

First, the total amounts of the soluble fractions of the EndoS mutant enzymes filtrated through the PVDF membrane were each applied to a glutathione sepharose 4B column equilibrated with PBS and the column was washed with 3 or more column volumes of PBS buffer. Subsequently, the GST-fused EndoS mutant enzyme was eluted with PBS buffer containing 10 mM glutathione in the reduced form and concentrated by ultrafiltration (Amicon Ultra-15 30K). After the concentration, the concentrate was separated on HiLoad 26/60 Superdex 200 pg column (GE Healthcare Bioscience) equilibrated with PBS to remove glutathione used for the elution and obtain the final purified sample. The yields of the EndoS mutant enzymes prepared in this way are shown in Table 2.

The obtained EndoS mutant enzyme solutions were prepared at 2 mg/mL and these were used for the measurement of hydrolysis and transglycosylation activities.

TABLE 2

Yield of EndoS mutant enzymes

| Mutant | Concentration (mg/mL) | Volume (mL) | Mutant | Concentration (mg/mL) | Volume (mL) |
|---|---|---|---|---|---|
| D233Q | 3.3 | 1.1 | D233Q/D405A | 7 | 0.13 |
| H122A/D233Q | 5 | 0.1 | D233Q/R406A | 5.6 | 0.9 |
| H122F/D233Q | 7.8 | 0.07 | D233Q/R406Q | 4 | 0.5 |
| P184Q/D233Q | 3.3 | 0.9 | D233Q/D279Q/Y282R | 3.3 | 0.4 |
| D233Q/D279S | 6.4 | 0.18 | D233Q/Y282R/D405A | 2.5 | 0.4 |
| D233Q/D279Q | 3 | 2.8 | D233Q/Q303L/Y348H | 2.8 | 1.1 |
| D233Q/Y282R | 4.3 | 0.5 | D233Q/Q303L/E350A | 2.1 | 1.3 |
| D233Q/Q303L | 4.3 | 2.6 | D233Q/Q303L/E350Q | 4 | 0.8 |
| D233Q/Y348H | 3.7 | 2.6 | D233Q/Q303L/E350D | 5.4 | 0.1 |
| D233Q/E350A | 3.8 | 0.8 | D233Q/Q303L/Y402F | 2.9 | 1.2 |
| D233Q/E350N | 2.7 | 0.8 | D233Q/Q303L/D405A | 5.9 | 0.5 |
| D233Q/E350Q | 4.6 | 2.6 | D233Q/Y348H/Y402F | 3.9 | 0.85 |
| D233Q/E350D | 4.2 | 2.6 | D233Q/E360A/Y402F | 3.9 | 0.8 |
| D233Q/Y402F | 4.4 | 2.8 | D233Q/E350A/R406A | 2.3 | 1 |
| D233Q/Y402W | 3.9 | 0.7 | D233Q/Y402F/D405A | 3.3 | 1.05 |

Example 2

Preparation of Reaction Solution of SG-Oxa (Compound of Structure in FIG. 1)

SG-Oxa used as a sugar donor in the following Examples was produced by the following process.

An aqueous solution (520 μl) of 2-chloro-1,3-dimethyl-1H-benzimidazol-3-ium chloride (CDMBI) (a product made by FUSHIMI Pharmaceutical Co., Ltd.) (53.7 mg, 245 μmol) was added to disialooctasaccharide (Tokyo Chemical Industry Co., Ltd., 100 mg, 49.5 μmol). To the reaction solution after cooling on ice, an aqueous solution (520 μl) of tripotassium phosphate (158 mg, 743 μmol) was added and the mixture was stirred on ice for 2 hours. The obtained reaction solution was ultrafiltered with Amicon Ultra (Ultracel 30K, a product made by Merck Millipore) to remove solid materials. The filtrate was purified by gel filtration chromatography. The apparatus used was Purif-Rp2 (a product made by Shoko Scientific Co., Ltd.), the column used was HiPrep 26/10 Desalting (a product made by GE Healthcare), the mobile phase used was a 0.03% —NH3 aqueous solution, the flow rate was 10 ml/min, and the fraction volume was 10 ml. The fractions containing the target product according to UV detection (220 nm) during elution were pooled together, a 0.1 N aqueous solution of sodium hydroxide (100 µl) was added to the pool, and the mixture was freeze-dried to obtain the target SG-Oxa as a colorless solid (87.0 mg, 43.4 µmol, 88% yield).

From the NMR chart of the obtained compound, it was confirmed to be the target compound (HELVETICA CHIMICA ACTA, 2012, 95, 1928-1936).

To the obtained SG-Oxa (1.19 mg) 50 mM tris buffer solution (pH 7.4) (23.8 µl) was added to prepare 50 mg/ml SG-Oxa solution (50 mM tris buffer solution pH 7.4). This was used for the measurement of transglycosylation activity.

Example 3

Preparation of (Fucα1,6)GlcNAc-Trastuzumab (Fucα1,6)GlcNAc-Trastuzumab to be used as an acceptor molecule in the transglycosylation reaction was produced by the following process.

A 1.18 mg/ml wild type EndoS solution (PBS) (10 µl) was added to an 11.3 mg/ml Trastuzumab (a product made by Genentech) solution (50 mM tris buffer solution pH 8.0) (2 ml) and the mixture was incubated at 30° C. for 5 hours. The progress of the reaction was confirmed using the Experion electrophoresis station. After the end of the reaction, purification by affinity chromatography and purification with a hydroxyapatite column were performed.

(1) Purification with affinity column
Purification apparatus: AKTA avant 25 (a product made by GE Healthcare)
Column: HiTrap Protein A HP column (5 ml) (a product made by GE Healthcare)
Flow rate: 5 ml/min (1 ml/min at the time of charge)

At the time of binding to the column, the reaction solution obtained as described above was added onto the top of the column, 1 CV of the binding buffer (20 mM phosphate buffer solution (pH 7.0)) was run at 1 ml/min, and further 5 CV was run at 5 ml/min. At the time of the intermediate washing, 15 CV of the washing solution (20 mM phosphate buffer solution (pH 7.0), 0.5 M sodium chloride solution) was run. At the time of elution, 6 CV of the elution buffer (ImmunoPure IgG Eution buffer, a product made by PIERCE) was run. The eluate was immediately neutralized with 1 M tris buffer solution (pH 9.0). The fractions detected by UV detection (280 nm) during elution were examined with the ultramicrospectrophotometer NanoDrop 1000 (a product made by Thermo Fisher Scientific) and the Experion electrophoresis station (a product made by BIO-RAD).

The fractions containing the target were concentrated with Amicon Ultra (Ultracel 30K, a product made by Merck Millipore) and buffer (5 mM phosphate buffer solution, 50 mM 2-morpholinoethanesulfonic acid (MES) solution, pH 6.8) exchange was conducted.

(2) Purification with hydroxyapatite column
Purification apparatus: AKTA avant25 (a product made by GE Healthcare)
Column: Bio-Scale Mini CHT Type I cartridge (5 ml) (a product made by BIO-RAD)
Flow rate: 5 ml/min (1 ml/min at the time of charge)

The solution obtained in (1) above was added onto the top of the column and 4 CV of Solution A (5 mM phosphate buffer solution, 50 mM 2-morpholinoethanesulfonic acid (MES), pH 6.8) was run. Then, elution was conducted using Solution A and Solution B (5 mM phosphate buffer solution, 50 mM 2-morpholinoethanesulfonic acid (MES), pH 6.8, 2 M sodium chloride solution). The elution conditions were Solution A:Solution B=100:0 to 0:100 (15 CV).

The fractions detected by UV detection (280 nm) during elution were examined with the ultramicrospectrophotometer NanoDrop 1000 (a product made by Thermo Fisher Scientific) and the Experion (™) electrophoresis station (BIO-RAD).

The fractions containing the target were concentrated using Amicon Ultra (Ultracel 30K, a product made by Merck Millipore) and buffer exchange to 50 mM phosphate buffer solution (pH 6.0) was conducted to obtain a 9.83 mg/ml (Fucα1,6)GlcNAc-Trastuzumab solution (phosphate buffer solution, pH 6.0) (1.8 ml). LC-MS:
calculated for the heavy chain of (Fuca', 6) GlcNAc-Trastuzumab, M=49497.86 found (m/z), 49497 (deconvolution data).
calculated for the light chain of (Fuca', 6) GlcNAc-Trastuzumab, M=23439.1, found (m/z), 23439.1 (deconvolution data).

Example 4

Measurement of Hydrolysis and Transglycosylation Activities of EndoS Mutant Enzymes (pH 7.4)

(4-1) Measurement of Hydrolysis Activity

The hydrolysis activity of the EndoS mutant enzymes on N297-linked sugar chains of commercially available Trastuzumab was measured as follows. A schematic view of the hydrolysis reaction is illustrated in FIG. 2.

A 20 mg/ml Trastuzumab solution to be used as a substrate solution for the hydrolysis reaction was prepared as follows. Otsuka distilled water (10 ml) was added to 100 mM tris buffer solution (pH7.4, a product made by CALBIOCHEM) (10 ml) to prepare 50 mM tris buffer solution (pH 7.4) (40 ml). To commercially available Trastuzumab (440 mg/vial, a product made by Genentech), the solubilization liquid (20 ml) attached thereto was added to prepare a Trastuzumab (ca. 21 mg/ml) solution. Ultrafiltration of the Trastuzumab (ca. 21 mg/ml) solution (2 ml) with Amicon Ultra (Ultracel 30K, a product made by Merck Millipore) was performed to displace the solvent with 50 mM tris buffer solution pH 7.4 prepared as described above and obtain the 20 mg/ml Trastuzumab solution (50 mM tris buffer solution pH 7.4).

To the substrate solution (25 µl) prepared as described above, the 2.0 mg/ml EndoS D233Q solution (5 µl) prepared in Example 1 was added and the mixture was incubated at 30° C. for 48 hours. At 1, 2, 4, 8, 24, and 48 hours after the onset of the reaction, a portion of this reaction solution was collected and the degree of progress of the reaction was measured using an Experion (™) electrophoresis station (BIO-RAD). For the measurement, measurement samples were prepared according to the protocol attached to the apparatus. In this process, the collected reaction solution is exposed to a solution containing dithiothreitol and heated at 95° C. for 5 minutes and the hydrolysis reaction is stopped immediately.

The obtained measurement samples were transferred to Experion (™) Pro260 Chips and measured according to the protocol attached to an Experion (™) electrophoresis station (BIO-RAD). From the obtained chromatogram, the unreacted substrate and the hydrolyzed product were confirmed as separated peaks. From the ratio of the peak areas of the unreacted substrate and the hydrolyzed product, the percent hydrolysis was calculated by the following calculation formula.

Percent hydrolysis (%)=[Peak area of H chain derived from (Fucα1,6)GlcNAc-Trastuzumab]/{[Peak area of H chain derived from commercially available Trastuzumab]+[Peak area of H chain derived from (Fucα1,6)GlcNAc-Trastuzumab]}×100

Similarly, the percent hydrolysis of the other EndoS mutant enzymes prepared in Example 1 at each reaction time was calculated (Table 3).

(4-2) Measurement of Transglycosylation Activity

The transglycosylation activity of the EndoS mutant enzymes produced in Example 1 was measured by the following method. SG-Oxa prepared in Example 2 and (Fucα1,6)GlcNAc-Trastuzumab prepared in Example 3 were used as the sugar donor and the acceptor molecule, respectively. A schematic view of transglycosylation reaction is illustrated in FIG. 3.

From the 9.83 mg/ml (Fucα1,6)GlcNAc-Trastuzumab solution (phosphate buffer solution, pH 6.0) prepared in Example 3, a 20 mg/ml (Fucα1,6)GlcNAc-Trastuzumab solution (50 mM tris buffer solution pH 7.4) was prepared according to a method similar to the preparation of the substrate solution as described in (4-1). To the 20 mg/ml (Fucα1,6)GlcNAc-Trastuzumab solution (50 mM tris buffer solution pH 7.4), the 50 mg/ml SG-Oxa solution (50 mM tris buffer solution pH 7.4) (1.07 µl) prepared in Example 2 and the 2.0 mg/ml EndoS D233Q solution (8 µl) prepared in Example 1 were added and the mixture was incubated at 30° C. for 48 hours. At the time points of 1, 2, 4, 8, 24, and 48 hours after the onset of the reaction, a portion of this reaction solution was collected and the degree of progress of the reaction was measured using an Experion (™) electrophoresis station. For the measurement, measurement samples were prepared according to the protocol attached to the apparatus. In this process, the collected reaction solution is exposed to a solution containing dithiothreitol and heated at 95° C. for 5 minutes and the transglycosylation reaction is stopped immediately.

The obtained measurement samples were transferred to Experion (™) Pro260 Chips and measured according to the protocol attached to an Experion (™) electrophoresis station (BIO-RAD). From the obtained chromatogram, the unreacted substrate and the transglycosylation product were confirmed as separated peaks. From the ratio of the peak areas of the unreacted substrate and the transglycosylation product, the percent transglycosylation was calculated by the following calculation formula.

Percent transglycosylation (%)=[Peak area of H chain derived from SG-Trastuzumab]/{[Peak area of H chain derived from (Fucα1,6)GlcNAc-Trastuzumab]+[Peak area of H chain derived from SG-Trastuzumab]}×100

Similarly, the percent transglycosylation of the other EndoS mutant enzymes prepared in Example 1 at each reaction time was calculated (Table 3).

SG-Trastuzumab, which is a transglycosylation product, was purified by a method similar to the purification of (FucU1,6)GlcNAc-Trastuzumab in Example 3. The obtained LC-MS analysis data of SG-Trastuzumab are shown below.

calculated for the heavy chain of SG-Trastuzumab, M=51500.6 Da; found (m/z), 51501 (deconvolution data).
calculated for the light chain of SG-Trastuzumab, M=23439.1 Da, found (m/z), 23439 (deconvolution data).

TABLE 3

Change over time of percent hydrolysis and percent transglycosylation of EndoS mutant enzymes (pH 7.4)

| Mutant | Percent hydrolysis (%) | | | | | | Percent transglycosylation (%) | | | | | |
|---|---|---|---|---|---|---|---|---|---|---|---|---|
| | 1 h | 2 h | 4 h | 8 h | 24 h | 48 h | 1 h | 2 h | 4 h | 8 h | 24 h | 48 h |
| D233Q | 0 | 11 | 17 | 30 | 55 | 71 | 52 | 83 | 82 | 80 | 75 | 66 |
| H122A/D233Q | 0 | 0 | 21 | 26 | 45 | 54 | 76 | 84 | 85 | 81 | 78 | 71 |
| H122F/D233Q | 0 | 0 | 0 | 0 | 0 | 0 | 3 | 8 | 13 | 28 | 52 | 60 |
| D233Q/D279S | 0 | 0 | 0 | 0 | 0 | 19 | 21 | 35 | 50 | 64 | 66 | 66 |
| D233Q/D279Q | 0 | 0 | 0 | 7 | 22 | 30 | 47 | 63 | 77 | 78 | 78 | 74 |
| D233Q/Q303L | 0 | 0 | 12 | 20 | 34 | 42 | 33 | 51 | 79 | 94 | 96 | 91 |
| D233Q/Y348H | 0 | 0 | 16 | 22 | 35 | 48 | 53 | 63 | 72 | 75 | 74 | 73 |
| D233Q/E350A | 0 | 0 | 0 | 12 | 28 | 32 | 48 | 69 | 86 | 91 | 89 | 87 |
| D233Q/E350N | 0 | 0 | 0 | 13 | 27 | 37 | 52 | 77 | 89 | 91 | 85 | 84 |
| D233Q/E350Q | 0 | 18 | 24 | 28 | 45 | 53 | 75 | 92 | 91 | 90 | 82 | 74 |
| D233Q/E350D | 0 | 0 | 0 | 12 | 25 | 32 | 49 | 66 | 82 | 89 | 89 | 88 |
| D233Q/Y402F | 0 | 0 | 0 | 0 | 0 | 15 | 36 | 49 | 66 | 77 | 82 | 82 |
| D233Q/D405A | 0 | 0 | 11 | 19 | 34 | 48 | 78 | 90 | 92 | 92 | 85 | 83 |
| D233Q/R406Q | 0 | 0 | 0 | 0 | 0 | 0 | 8 | 14 | 23 | 33 | 48 | 53 |
| D233Q/Y282R/D405A | 0 | 0 | 0 | 0 | 0 | 0 | 16 | 25 | 41 | 56 | 66 | 71 |
| D233Q/Q303L/E350A | 0 | 0 | 0 | 0 | 0 | 0 | 5 | 9 | 13 | 24 | 42 | 49 |
| D233Q/Q303L/E350Q | 0 | 0 | 0 | 0 | 0 | 12 | 15 | 33 | 50 | 69 | 87 | 92 |
| D233Q/Q303L/E350D | 0 | 0 | 0 | 0 | 0 | 0 | 5 | 12 | 21 | 34 | 58 | 66 |
| D233Q/Q303L/Y402F | 0 | 0 | 0 | 0 | 0 | 0 | 5 | 9 | 15 | 27 | 44 | 52 |
| D233Q/Q303L/D405A | 0 | 0 | 0 | 0 | 0 | 0 | 10 | 19 | 30 | 43 | 63 | 72 |
| D233Q/Y402F/D405A | 0 | 0 | 0 | 0 | 0 | 0 | 12 | 22 | 39 | 55 | 72 | 77 |

The invention claimed is:

1. An EndoS mutant enzyme comprising the amino acid sequence of amino acid numbers 37 to 995 of the amino acid sequence of SEQ ID NO: 2 with a mutation only at an amino acid position selected from the group consisting of: amino acid 122, amino acid 184, amino acid 279, amino acid 282, amino acid 303, amino acid 348, amino acid 350, amino acid 402, amino acid 405, amino acid 406, and a combination thereof, wherein said EndoS mutant enzyme exhibits a reduced hydrolysis activity in comparison with the hydrolysis activity of an EndoS D233Q mutant enzyme, the activity being an activity on an N-linked sugar chain (N297 linked sugar chain) linked to Asn at position 297 in IgG.

2. The EndoS mutant enzyme according to claim 1, wherein the mutation is at 1 to 4 amino acid positions selected from the group consisting of: 122, 184, 279, 282, 303, 348, 350, 402, 405, and 406.

3. The EndoS mutant enzyme according to claim 1, wherein the mutation is a mutation at one amino acid position selected from the group consisting of 303, 350, and 405.

4. The EndoS mutant enzyme according to claim 1, wherein the mutation is at least one selected from the group consisting of:

a mutation at 122 to the amino acids: Gly, Cys, Thr, Ser, Val, Pro, Ala, Glu, Asp, Leu, Ile, Met, or Phe;

a mutation at 184 to the amino acids: Gly, Cys, Thr, Ser, Val, Ala, Gln, or Asn;

a mutation at 279 to the amino acids: Gly, Cys, Thr, Ser, Val, Pro, Ala, or Gln;

a mutation at 282 to the amino acids: Arg, Lys, or His;

a mutation at 303 to the amino acids: Met, Pro, or Leu;

a mutation at 348 to the amino acids: His or Trp;

a mutation at 350 to the amino acids: Lys, Arg, His, Tyr, Gln, Asn, Asp, Gly, Cys, Thr, Ser, Val, Pro, or Ala;

a mutation at 402 to the amino acids: Phe or Trp;

a mutation at 405 to the amino acids: Gly, Cys, Thr, Ser, Val, Pro, or Ala; and a mutation at 406 to the amino acids: Gly, Cys, Thr, Ser, Val, Pro, Ala, Glu, Asp, Gln, or Asn.

5. The EndoS mutant enzyme according to claim 4, wherein the mutation is at least one selected from the group consisting of:

a mutation at H122 to Ala (H122A) or Phe (H122F);

a mutation at P184 to Gln (P184Q);

a mutation at D279 to Ser (D279S) or Gln (D2790);

a mutation at Y282 to Arg (Y282R);

a mutation at 0303 to Leu (0303L);

a mutation at Y348 to His (Y348H);

a mutation at E350 to Ala (E350A), Asn (E350N), Asp (E350D), or Gln (E3500);

a mutation at Y402 to Phe (Y402F) or Trp (Y402W);

a mutation at D405 to Ala (D405A); and a mutation at R406 to Gln (R4060).

6. The EndoS mutant enzyme according to claim 5, comprising at least one mutation selected from the group consisting of 0303L, E350A, E35N, E350D, E350Q, and D405A.

7. The EndoS mutant enzyme according to claim 6, wherein the mutation is 0303L, E350A, E350N, E350D, E350Q, D405A, H122A/0303L, H122F/0303L, P184Q/0303L, D279Q/0303L, D279S/0303L, Y282R/0303L, 0303L/Y348H, 0303L/E350A, 0303L/E350N, 0303L/E350D, 0303L/E3500, 0303L/Y402F, 0303L/Y402W, 0303L/D405A, 0303L/R4060, H122A/E350A, H122F/E350A, P1840/E350A, D279Q/E350A, D279S/E350A, Y282R/E350A, Y348HZE350A, E350A/Y402F, E350A/Y402W, E350A/D405A, E350A/R4060, H122A/E350N, H122F/E350N, P1840/E350N, D2790/E350N, D279S/E350N, Y282R/E350N, Y348H/E350N, E350N/Y402F, E350N/Y402W, E350N/D405A, E350N/R4060, H122A/E350D, H122F/E350D, P184Q/E350D, D2790/E350D, D279S/E350D, Y282R/E350D, Y348H/E350D, E350D/Y402F, E350D/Y402W, E350D/D405A, E350D/R4060, H122A/E350Q, H122F/E350Q, P1840/E350Q, D279Q/E350Q, D279S/E3500, Y282R/E350Q, E3500/Y348H, E3500/Y402F, E3500/Y402W, E3500/D405A, E350Q/R4060, H122A/D405A, H122F/D405A, P1840/D405A, D279Q/D405A, D279S/D405A, Y282R/D405A, Y348H/D40 5A, or D405A/R4060.

8. The EndoS mutant enzyme according to claim 7, wherein the mutation is 0303L, E350A, E350N, E350D, E350Q, D405A, 0303L/E350A, 0303L/E350N, 0303L/E350D, 0303L/E35010, 0303L/D405A, E350A/D405A, E350N/D405A, E350D/D405A, or E3500/D405A.

9. The EndoS mutant enzyme according to claim 4, wherein the mutation is H122A, H122F, P1840, D2790, D279S, Y282R, Y348H, Y402F, Y402W, or R4060.

10. A polynucleotide encoding the EndoS mutant enzyme according to claim 1.

11. A vector comprising a nucleotide complementary to the polynucleotide according to claim 10.

12. A host cell transformed with the vector according to claim 11.

13. A method of production of a molecule comprising a sugar-remodeled Fc region, comprising reacting a molecule comprising an Fc region of IgG having a core GlcNAc optionally with fucose addition as an N297-linked sugar chain with a sugar donor having a structure comprising oxazolinated GlcNAc in the presence of the EndoS mutant enzyme according to claim 1 to produce a molecule comprising an Fc region with a N297-linked sugar chain having a structure in which a sugar chain possessed by the sugar donor is transferred to the core GlcNAc of the N297-linked sugar chain.

14. The method of production according to claim 13, wherein the molecule comprising an Fc region is an IgG monoclonal antibody.

* * * * *

SEQUENCE LISTING

<160> NUMBER OF SEQ ID NOS: 9

<210> SEQ ID NO 1
<211> LENGTH: 995
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 1

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335
```

```
Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
        370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
            450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
            530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
            610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
            690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
```

```
                    755                 760                 765

Ala Glu Gly Ala Thr Val Ile Gly Gly Ser Ala Asp Pro Val Asn Ala
        770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 2
<211> LENGTH: 995
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: Novel mutants of Endo-S D233Q having at least
      one mutation other than D233Q.
<220> FEATURE:
<221> NAME/KEY: mutation
<222> LOCATION: (122)..(122)
<223> OTHER INFORMATION: The amino acid is His in wild type EndoS and
      can be mutated.
<220> FEATURE:
<221> NAME/KEY: mutation
<222> LOCATION: (184)..(184)
<223> OTHER INFORMATION: The amino acid is Pro in wild type EndoS and
      can be mutated.
<220> FEATURE:
<221> NAME/KEY: mutation
<222> LOCATION: (187)..(187)
<223> OTHER INFORMATION: The amino acid is Phe in wild type EndoS and
      can be mutated.
<220> FEATURE:
<221> NAME/KEY: mutation
<222> LOCATION: (279)..(279)
<223> OTHER INFORMATION: The amino acid is Asp in wild type EndoS and
      can be mutated.
```

```
<220> FEATURE:
<221> NAME/KEY: mutation
<222> LOCATION: (281)..(281)
<223> OTHER INFORMATION: The amino acid is Thr in wild type EndoS and
      can be mutated.
<220> FEATURE:
<221> NAME/KEY: mutation
<222> LOCATION: (282)..(282)
<223> OTHER INFORMATION: The amino acid is Tyr in wild type EndoS and
      can be mutated.
<220> FEATURE:
<221> NAME/KEY: mutation
<222> LOCATION: (303)..(303)
<223> OTHER INFORMATION: The amino acid is Gln in wild type EndoS and
      can be mutated.
<220> FEATURE:
<221> NAME/KEY: mutation
<222> LOCATION: (348)..(348)
<223> OTHER INFORMATION: The amino acid is Tyr in wild type EndoS and
      can be mutated.
<220> FEATURE:
<221> NAME/KEY: mutation
<222> LOCATION: (350)..(350)
<223> OTHER INFORMATION: The amino acid is Glu in wild type EndoS and
      can be mutated.
<220> FEATURE:
<221> NAME/KEY: mutation
<222> LOCATION: (402)..(402)
<223> OTHER INFORMATION: The amino acid is Tyr in wild type EndoS and
      can be mutated.
<220> FEATURE:
<221> NAME/KEY: mutation
<222> LOCATION: (405)..(405)
<223> OTHER INFORMATION: The amino acid is Asp in wild type EndoS and
      can be mutated.
<220> FEATURE:
<221> NAME/KEY: mutation
<222> LOCATION: (406)..(406)
<223> OTHER INFORMATION: The amino acid is Arg in wild type EndoS and
      can be mutated.

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp Xaa Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Xaa Trp Arg Xaa Leu Ala Gly Gly Asp
            180                 185                 190
```

```
Asn Ser Gly Ile Ala Glu Asp Thr Ser Lys Tyr Pro Asn Thr Pro Glu
            195                 200                 205

Gly Asn Lys Ala Leu Ala Lys Ala Ile Val Asp Glu Tyr Val Tyr Lys
210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Xaa Ser Xaa Xaa Met Ala Asp Lys Asn Pro
        275                 280                 285

Leu Ile Glu Arg Gly Ala Pro Tyr Ile Asn Leu Leu Leu Val Xaa Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Xaa Glu Xaa Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Val Lys Gly Gly Ile Phe
385                 390                 395                 400

Ser Xaa Ala Ile Xaa Xaa Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
```

```
              610                 615                 620
Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                    645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
                    675                 680                 685

Lys Ile Ala Gly Arg Ser Phe Val Asp Ser Asn Tyr His Tyr Asn Asn
690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                    725                 730                 735

Tyr Lys Val Asp Phe Phe Ser Pro Ala Asp Lys Thr Lys Ala Val His
                740                 745                 750

Thr Ala Lys Val Ile Val Gly Asp Glu Lys Thr Met Met Val Asn Leu
                755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                    805                 810                 815

Gly Leu Ile Lys His Trp Arg Phe Phe Asn Asp Ser Ala Arg Asn Pro
                820                 825                 830

Glu Thr Thr Asn Lys Pro Ile Gln Glu Ala Ser Leu Gln Ile Phe Asn
                    835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                    885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
                    915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                    965                 970                 975

Asn Ala Asn Ala Gly Val Leu Lys Asp Cys Ile Glu Lys Arg Gln Leu
                980                 985                 990

Leu Lys Lys
        995

<210> SEQ ID NO 3
<211> LENGTH: 2985
<212> TYPE: DNA
<213> ORGANISM: Artificial Sequence
```

<220> FEATURE:
<223> OTHER INFORMATION: Synthetic
<220> FEATURE:
<221> NAME/KEY: misc_feature
<222> LOCATION: (1)..(2985)
<223> OTHER INFORMATION: cDNA of EndoS D233Q

<400> SEQUENCE: 3

| | | | | | |
|---|---|---|---|---|---|
| atggacaaac | atctgctggt | taaacgtacc | ctggggttgtg | tttgtgcagc | aaccctgatg | 60 |
| ggtgcagcac | tggcaaccca | tcatgatagc | ctgaataccg | ttaaagcaga | agaaaaaacc | 120 |
| gttcaggttc | agaaaggtct | gccgagcatt | gatagtctgc | attatctgag | cgaaaacagc | 180 |
| aaaaaagaat | ttaaagaaga | actgagcaaa | gccggtcaag | aaagccagaa | agttaaagaa | 240 |
| attctggcaa | aagcacagca | ggcagataaa | caggcacaag | aactggccaa | aatgaaaatc | 300 |
| ccggaaaaaa | ttccgatgaa | accgctgcat | ggtccgctgt | atggtggtta | ttttcgtacc | 360 |
| tggcatgata | aaccagcga | tccgaccgaa | aaagataaag | ttaatagcat | gggtgaactg | 420 |
| ccgaaagaag | ttgatctggc | atttatcttt | cacgactgga | ccaaagatta | tagcctgttt | 480 |
| tggaaagaac | tggcgaccaa | acatgttccg | aaactgaata | acagggcac | ccgtgttatt | 540 |
| cgtaccattc | cgtggcgttt | tctggcaggc | ggtgataata | gcggtattgc | agaagatacc | 600 |
| agcaaatatc | cgaatacacc | ggaaggtaat | aaagcactgg | cgaaagcaat | tgtggatgag | 660 |
| tatgtgtata | atacaatct | ggatggcctg | gatgttcaag | ttgaacatga | tagcattccg | 720 |
| aaagtggaca | aaaagagga | taccgcaggc | gttgaacgta | gcattcaggt | ttttgaagaa | 780 |
| atcggcaaac | tgattggtcc | gaaaggtgtt | gataaaagcc | gtctgtttat | tatggatagc | 840 |
| acctatatgg | ccgataaaaa | cccgctgatt | gaacgtggtg | caccgtatat | taacctgctg | 900 |
| ctggttcagg | tttatggtag | ccagggtgaa | aaaggtggtt | gggaaccggt | tagcaatcgt | 960 |
| cctgaaaaaa | ccatggaaga | acgttggcag | ggttatagca | aatatatccg | tccggaacag | 1020 |
| tatatgatcg | gctttagctt | ttatgaagaa | aatgcccaag | agggcaatct | gtggtatgat | 1080 |
| attaacagcc | gtaaagatga | ggataaagcc | aatggcatta | acaccgatat | caccggtaca | 1140 |
| cgtgcagaac | gttatgcccg | ttggcagccg | aaaaccggtg | gtgttaaagg | tggtatttt | 1200 |
| agctatgcca | ttgatcgtga | tggtgttgca | catcaaccga | aaaatacgc | caaacagaaa | 1260 |
| gagttcaaag | acgccaccga | taacattttc | catagcgatt | atagcgttag | caaagccctg | 1320 |
| aaaaccgtga | tgctgaaaga | caaaagctat | gatctgatcg | acgagaaaga | ttttccggat | 1380 |
| aaagcgctgc | gtgaagcagt | tatggcacag | gttggcaccc | gtaaaggtga | tctggaacgt | 1440 |
| tttaatggca | ccctgcgtct | ggataatccg | gcaattcaga | gcctggaagg | tctgaacaaa | 1500 |
| ttcaaaaaac | tggcacagct | ggatctgatt | ggcctgagcc | gtattaccaa | actggatcgt | 1560 |
| agcgttctgc | ctgcaaatat | gaaaccgggt | aaagatacce | tggaaccgt | tctgaaaacc | 1620 |
| tacaaaaaag | acaacaaaga | agaaccggca | accattccgc | tgttagcct | gaaagttagc | 1680 |
| ggtctgaccg | gtctgaaaga | gctggacctg | tcaggttttg | atcgcgaaac | cctggcaggt | 1740 |
| ctggatgcag | ccacactgac | cagcctggaa | aaagttgata | ttagcggcaa | taaactggac | 1800 |
| ctggcaccgg | gtacagaaaa | tcgtcagatc | ttcgatacca | tgctgagcac | cattagcaat | 1860 |
| catgttggta | gcaatgaaca | gaccgtgaaa | tttgataaac | agaaaccgac | cggtcattat | 1920 |
| cctgataccc | atggtaaaac | cagtctgcgt | ctgccggttg | caaatgaaaa | agtggatctg | 1980 |
| cagagccagc | tgctgtttgg | caccgttacc | aatcagggca | cactgattaa | tagcgaagca | 2040 |
| gattataaag | cctatcagaa | ccataaaatt | gccggtcgta | gctttgtgga | tagcaactac | 2100 |

-continued

```
cattacaaca acttcaaagt gagctacgag aactataccg tgaaagttac cgatagcacc    2160
ctgggcacca ccacagataa aacactggcc acggataaag aggaaaccta taaagtcgat    2220 ttttttcagcc ctgccgacaa aaccaaagca gttcataccg caaaagttat cgtgggtgat   2280
gaaaaaacga tgatggttaa tctggcagaa ggtgcaaccg ttattggtgg tagcgcagat    2340
ccggttaatg cacgtaaagt tttttgatggt cagctgggta gcgaaaccga taatatcagc   2400
ctgggttggg atagcaaaca gagcattatc tttaaactga agaggacgg cctgattaaa     2460 cattggcgct ttttttaacga tagcgcacgt aatccggaaa ccacaaataa accgattcaa   2520
gaagcaagcc tgcagatttt taacatcaaa gattacaacc tggacaacct gctggaaaac   2580
ccgaacaaat ttgatgatga aaatactgg attaccgtgg ataccatag cgcacagggt    2640 gaacgtgcaa ccgcatttag caataccctg aataatatca cgagcaaata ttggcgtgtg   2700
gtgtttgata ccaaaggcga tcgttatagc agtccggttg tgccggaact gcagattctg   2760
ggttatccgc tgccgaatgc agataccatt atgaaaacag ttaccaccgc caagaactg    2820 tcacagcaga aagacaaatt tagccagaaa atgctggacg aactgaaaat caagaaatg    2880 gcactggaaa ccagcctgaa ctccaaaatt ttcgatgtta ccgccattaa tgcaaatgcc   2940
ggtgttctga aagattgcat tgaaaaacgt cagctgctga aaaaa                   2985
```

<210> SEQ ID NO 4
<211> LENGTH: 995
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 4

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190
```

```
Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Leu Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Arg Trp Gln Gly Tyr Ser Lys Tyr Ile
                325                 330                 335

Arg Pro Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605
```

```
Gln Ile Phe Asp Thr Met Leu Ser Thr Ile Ser Asn His Val Gly Ser
610                 615                 620
Asn Glu Gln Thr Val Lys Phe Asp Lys Gln Lys Pro Thr Gly His Tyr
625                 630                 635                 640
Pro Asp Thr Tyr Gly Lys Thr Ser Leu Arg Leu Pro Val Ala Asn Glu
                645                 650                 655
Lys Val Asp Leu Gln Ser Gln Leu Leu Phe Gly Thr Val Thr Asn Gln
            660                 665                 670
Gly Thr Leu Ile Asn Ser Glu Ala Asp Tyr Lys Ala Tyr Gln Asn His
        675                 680                 685
Lys Ile Ala Gly Arg Ser Phe Val Asp Ser Asn Tyr His Tyr Asn Asn
690                 695                 700
Phe Lys Val Ser Tyr Glu Asn Tyr Thr Val Lys Val Thr Asp Ser Thr
705                 710                 715                 720
Leu Gly Thr Thr Thr Asp Lys Thr Leu Ala Thr Asp Lys Glu Glu Thr
                725                 730                 735
Tyr Lys Val Asp Phe Phe Ser Pro Ala Asp Lys Thr Lys Ala Val His
            740                 745                 750
Thr Ala Lys Val Ile Val Gly Asp Glu Lys Thr Met Met Val Asn Leu
        755                 760                 765
Ala Glu Gly Ala Thr Val Ile Gly Gly Ser Ala Asp Pro Val Asn Ala
770                 775                 780
Arg Lys Val Phe Asp Gly Gln Leu Gly Ser Glu Thr Asp Asn Ile Ser
785                 790                 795                 800
Leu Gly Trp Asp Ser Lys Gln Ser Ile Ile Phe Lys Leu Lys Glu Asp
                805                 810                 815
Gly Leu Ile Lys His Trp Arg Phe Phe Asn Asp Ser Ala Arg Asn Pro
            820                 825                 830
Glu Thr Thr Asn Lys Pro Ile Gln Glu Ala Ser Leu Gln Ile Phe Asn
        835                 840                 845
Ile Lys Asp Tyr Asn Leu Asp Asn Leu Leu Glu Asn Pro Asn Lys Phe
850                 855                 860
Asp Asp Glu Lys Tyr Trp Ile Thr Val Asp Thr Tyr Ser Ala Gln Gly
865                 870                 875                 880
Glu Arg Ala Thr Ala Phe Ser Asn Thr Leu Asn Asn Ile Thr Ser Lys
                885                 890                 895
Tyr Trp Arg Val Val Phe Asp Thr Lys Gly Asp Arg Tyr Ser Ser Pro
            900                 905                 910
Val Val Pro Glu Leu Gln Ile Leu Gly Tyr Pro Leu Pro Asn Ala Asp
        915                 920                 925
Thr Ile Met Lys Thr Val Thr Thr Ala Lys Glu Leu Ser Gln Gln Lys
930                 935                 940
Asp Lys Phe Ser Gln Lys Met Leu Asp Glu Leu Lys Ile Lys Glu Met
945                 950                 955                 960
Ala Leu Glu Thr Ser Leu Asn Ser Lys Ile Phe Asp Val Thr Ala Ile
                965                 970                 975
Asn Ala Asn Ala Gly Val Leu Lys Asp Cys Ile Glu Lys Arg Gln Leu
            980                 985                 990
Leu Lys Lys
        995

<210> SEQ ID NO 5
<211> LENGTH: 995
<212> TYPE: PRT
```

<210> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 5

```
Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Leu Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Gln Asn Ala
            340                 345                 350

Gln Glu Gly Asn Leu Trp Tyr Asp Ile Asn Ser Arg Lys Asp Glu Asp
        355                 360                 365
```

```
Lys Ala Asn Gly Ile Asn Thr Asp Ile Thr Gly Thr Arg Ala Glu Arg
    370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
                435                 440                 445

Ser Tyr Asp Leu Ile Asp Glu Lys Asp Phe Pro Asp Lys Ala Leu Arg
450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
                500                 505                 510

Ser Arg Ile Thr Lys Leu Asp Arg Ser Val Leu Pro Ala Asn Met Lys
                515                 520                 525

Pro Gly Lys Asp Thr Leu Glu Thr Val Leu Glu Thr Tyr Lys Lys Asp
            530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
                595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
                675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
                740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
```

```
                                  785                 790                 795                 800
    Leu Gly Trp Asp Ser Lys Gln Ser Ile Ile Phe Lys Leu Lys Glu Asp
                    805                 810                 815

Gly Leu Ile Lys His Trp Arg Phe Phe Asn Asp Ser Ala Arg Asn Pro
                820                 825                 830

Glu Thr Thr Asn Lys Pro Ile Gln Glu Ala Ser Leu Gln Ile Phe Asn
                835                 840                 845

Ile Lys Asp Tyr Asn Leu Asp Asn Leu Leu Glu Asn Pro Asn Lys Phe
            850                 855                 860

Asp Asp Glu Lys Tyr Trp Ile Thr Val Asp Thr Tyr Ser Ala Gln Gly
    865                 870                 875                 880

Glu Arg Ala Thr Ala Phe Ser Asn Thr Leu Asn Asn Ile Thr Ser Lys
                    885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
            915                 920                 925

Thr Ile Met Lys Thr Val Thr Thr Ala Lys Glu Leu Ser Gln Gln Lys
        930                 935                 940

Asp Lys Phe Ser Gln Lys Met Leu Asp Glu Leu Lys Ile Lys Glu Met
    945                 950                 955                 960

Ala Leu Glu Thr Ser Leu Asn Ser Lys Ile Phe Asp Val Thr Ala Ile
                    965                 970                 975

Asn Ala Asn Ala Gly Val Leu Lys Asp Cys Ile Glu Lys Arg Gln Leu
                980                 985                 990

Leu Lys Lys
            995

<210> SEQ ID NO 6
<211> LENGTH: 995
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 6

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125
```

```
Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Leu Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400

Ser Tyr Ala Ile Ala Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
```

```
               545                 550                 555                 560
     Gly Leu Thr Gly Leu Lys Glu Leu Asp Leu Ser Gly Phe Asp Arg Glu
                     565                 570                 575

Thr Leu Ala Gly Leu Asp Ala Ala Thr Leu Thr Ser Leu Glu Lys Val
                     580                 585                 590

Asp Ile Ser Gly Asn Lys Leu Asp Leu Ala Pro Gly Thr Glu Asn Arg
                     595                 600                 605

Gln Ile Phe Asp Thr Met Leu Ser Thr Ile Ser Asn His Val Gly Ser
                     610                 615                 620

Asn Glu Gln Thr Val Lys Phe Asp Lys Gln Lys Pro Thr Gly His Tyr
     625                 630                 635                 640

Pro Asp Thr Tyr Gly Lys Thr Ser Leu Arg Leu Pro Val Ala Asn Glu
                     645                 650                 655

Lys Val Asp Leu Gln Ser Gln Leu Leu Phe Gly Thr Val Thr Asn Gln
                     660                 665                 670

Gly Thr Leu Ile Asn Ser Glu Ala Asp Tyr Lys Ala Tyr Gln Asn His
                     675                 680                 685

Lys Ile Ala Gly Arg Ser Phe Val Asp Ser Asn Tyr His Tyr Asn Asn
     690                 695                 700

Phe Lys Val Ser Tyr Glu Asn Tyr Thr Val Lys Val Thr Asp Ser Thr
     705                 710                 715                 720

Leu Gly Thr Thr Thr Asp Lys Thr Leu Ala Thr Asp Lys Glu Glu Thr
                     725                 730                 735

Tyr Lys Val Asp Phe Phe Ser Pro Ala Asp Lys Thr Lys Ala Val His
                     740                 745                 750

Thr Ala Lys Val Ile Val Gly Asp Glu Lys Thr Met Met Val Asn Leu
                     755                 760                 765

Ala Glu Gly Ala Thr Val Ile Gly Gly Ser Ala Asp Pro Val Asn Ala
                     770                 775                 780

Arg Lys Val Phe Asp Gly Gln Leu Gly Ser Glu Thr Asp Asn Ile Ser
     785                 790                 795                 800

Leu Gly Trp Asp Ser Lys Gln Ser Ile Ile Phe Lys Leu Lys Glu Asp
                     805                 810                 815

Gly Leu Ile Lys His Trp Arg Phe Phe Asn Asp Ser Ala Arg Asn Pro
                     820                 825                 830

Glu Thr Thr Asn Lys Pro Ile Gln Glu Ala Ser Leu Gln Ile Phe Asn
                     835                 840                 845

Ile Lys Asp Tyr Asn Leu Asp Asn Leu Leu Glu Asn Pro Asn Lys Phe
     850                 855                 860

Asp Asp Glu Lys Tyr Trp Ile Thr Val Asp Thr Tyr Ser Ala Gln Gly
     865                 870                 875                 880

Glu Arg Ala Thr Ala Phe Ser Asn Thr Leu Asn Asn Ile Thr Ser Lys
                     885                 890                 895

Tyr Trp Arg Val Val Phe Asp Thr Lys Gly Asp Arg Tyr Ser Ser Pro
                     900                 905                 910

Val Val Pro Glu Leu Gln Ile Leu Gly Tyr Pro Leu Pro Asn Ala Asp
                     915                 920                 925

Thr Ile Met Lys Thr Val Thr Thr Ala Lys Glu Leu Ser Gln Gln Lys
                     930                 935                 940

Asp Lys Phe Ser Gln Lys Met Leu Asp Glu Leu Lys Ile Lys Glu Met
     945                 950                 955                 960

Ala Leu Glu Thr Ser Leu Asn Ser Lys Ile Phe Asp Val Thr Ala Ile
                     965                 970                 975
```

Asn Ala Asn Ala Gly Val Leu Lys Asp Cys Ile Glu Lys Arg Gln Leu
            980                 985                 990

Leu Lys Lys
        995

<210> SEQ ID NO 7
<211> LENGTH: 995
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 7

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg

-continued

```
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Gln Asn Ala
                340                 345                 350

Gln Glu Gly Asn Leu Trp Tyr Asp Ile Asn Ser Arg Lys Asp Glu Asp
                355                 360                 365

Lys Ala Asn Gly Ile Asn Thr Asp Ile Thr Gly Thr Arg Ala Glu Arg
                370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
                435                 440                 445

Ser Tyr Asp Leu Ile Asp Glu Lys Asp Phe Pro Asp Lys Ala Leu Arg
                450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
                500                 505                 510

Ser Arg Ile Thr Lys Leu Asp Arg Ser Val Leu Pro Ala Asn Met Lys
                515                 520                 525

Pro Gly Lys Asp Thr Leu Glu Thr Val Leu Glu Thr Tyr Lys Lys Asp
                530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
                595                 600                 605

Gln Ile Phe Asp Thr Met Leu Ser Thr Ile Ser Asn His Val Gly Ser
                610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
                675                 680                 685

Lys Ile Ala Gly Arg Ser Phe Val Asp Ser Asn Tyr His Tyr Asn Asn
                690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735
```

Tyr Lys Val Asp Phe Ser Pro Ala Asp Lys Thr Lys Ala Val His
              740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
            835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
            915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 8
<211> LENGTH: 995
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 8

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu

```
              65                  70                  75                  80

Ile Leu Ala Lys Ala Gln Gln Ala Asp Lys Gln Ala Gln Glu Leu Ala
                     85                  90                  95

Lys Met Lys Ile Pro Glu Lys Ile Pro Met Lys Pro Leu His Gly Pro
                    100                 105                 110

Leu Tyr Gly Gly Tyr Phe Arg Thr Trp His Asp Lys Thr Ser Asp Pro
                    115                 120                 125

Thr Glu Lys Asp Lys Val Asn Ser Met Gly Glu Leu Pro Lys Glu Val
                130                 135                 140

Asp Leu Ala Phe Ile Phe His Asp Trp Thr Lys Asp Tyr Ser Leu Phe
    145                 150                 155                 160

Trp Lys Glu Leu Ala Thr Lys His Val Pro Lys Leu Asn Lys Gln Gly
                    165                 170                 175

Thr Arg Val Ile Arg Thr Ile Pro Trp Arg Phe Leu Ala Gly Gly Asp
                    180                 185                 190

Asn Ser Gly Ile Ala Glu Asp Thr Ser Lys Tyr Pro Asn Thr Pro Glu
                    195                 200                 205

Gly Asn Lys Ala Leu Ala Lys Ala Ile Val Asp Glu Tyr Val Tyr Lys
                210                 215                 220

Tyr Asn Leu Asp Gly Leu Asp Val Gln Val Glu His Asp Ser Ile Pro
    225                 230                 235                 240

Lys Val Asp Lys Glu Asp Thr Ala Gly Val Glu Arg Ser Ile Gln
                    245                 250                 255

Val Phe Glu Glu Ile Gly Lys Leu Ile Gly Pro Lys Gly Val Asp Lys
                    260                 265                 270

Ser Arg Leu Phe Ile Met Asp Ser Thr Tyr Met Ala Asp Lys Asn Pro
                    275                 280                 285

Leu Ile Glu Arg Gly Ala Pro Tyr Ile Asn Leu Leu Val Gln Val
                    290                 295                 300

Tyr Gly Ser Gln Gly Glu Lys Gly Gly Trp Glu Pro Val Ser Asn Arg
    305                 310                 315                 320

Pro Glu Lys Thr Met Glu Glu Arg Trp Gln Gly Tyr Ser Lys Tyr Ile
                    325                 330                 335

Arg Pro Glu Gln Tyr Met Ile Gly Phe Ser Phe Tyr Glu Glu Asn Ala
                    340                 345                 350

Gln Glu Gly Asn Leu Trp Tyr Asp Ile Asn Ser Arg Lys Asp Glu Asp
                    355                 360                 365

Lys Ala Asn Gly Ile Asn Thr Asp Ile Thr Gly Thr Arg Ala Glu Arg
                370                 375                 380

Tyr Ala Arg Trp Gln Pro Lys Thr Gly Gly Val Lys Gly Gly Ile Phe
    385                 390                 395                 400

Ser Tyr Ala Ile Ala Arg Asp Gly Val Ala His Gln Pro Lys Lys Tyr
                    405                 410                 415

Ala Lys Gln Lys Glu Phe Lys Asp Ala Thr Asp Asn Ile Phe His Ser
                    420                 425                 430

Asp Tyr Ser Val Ser Lys Ala Leu Lys Thr Val Met Leu Lys Asp Lys
                    435                 440                 445

Ser Tyr Asp Leu Ile Asp Glu Lys Asp Phe Pro Asp Lys Ala Leu Arg
                    450                 455                 460

Glu Ala Val Met Ala Gln Val Gly Thr Arg Lys Gly Asp Leu Glu Arg
    465                 470                 475                 480

Phe Asn Gly Thr Leu Arg Leu Asp Asn Pro Ala Ile Gln Ser Leu Glu
                    485                 490                 495
```

```
Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
            530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
            565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
            610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
            645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
            690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
            725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
            770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
            805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
            835                 840                 845

Ile Lys Asp Tyr Asn Leu Asp Asn Leu Leu Glu Asn Pro Asn Lys Phe
            850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
            885                 890                 895

Tyr Trp Arg Val Val Phe Asp Thr Lys Gly Asp Arg Tyr Ser Ser Pro
            900                 905                 910
```

```
Val Val Pro Glu Leu Gln Ile Leu Gly Tyr Pro Leu Pro Asn Ala Asp
            915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 9
<211> LENGTH: 995
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(995)
<223> OTHER INFORMATION: D233Q mutant of Endo-S

<400> SEQUENCE: 9

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255
```

```
Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400

Ser Phe Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670
```

```
Gly Thr Leu Ile Asn Ser Glu Ala Asp Tyr Lys Ala Tyr Gln Asn His
            675             680             685

Lys Ile Ala Gly Arg Ser Phe Val Asp Ser Asn Tyr His Tyr Asn Asn
            690             695             700

Phe Lys Val Ser Tyr Glu Asn Tyr Thr Val Lys Val Thr Asp Ser Thr
705             710             715             720

Leu Gly Thr Thr Thr Asp Lys Thr Leu Ala Thr Asp Lys Glu Glu Thr
                725             730             735

Tyr Lys Val Asp Phe Phe Ser Pro Ala Asp Lys Thr Lys Ala Val His
            740             745             750

Thr Ala Lys Val Ile Val Gly Asp Glu Lys Thr Met Met Val Asn Leu
            755             760             765

Ala Glu Gly Ala Thr Val Ile Gly Gly Ser Ala Asp Pro Val Asn Ala
            770             775             780

Arg Lys Val Phe Asp Gly Gln Leu Gly Ser Glu Thr Asp Asn Ile Ser
785             790             795             800

Leu Gly Trp Asp Ser Lys Gln Ser Ile Ile Phe Lys Leu Lys Glu Asp
                805             810             815

Gly Leu Ile Lys His Trp Arg Phe Phe Asn Asp Ser Ala Arg Asn Pro
            820             825             830

Glu Thr Thr Asn Lys Pro Ile Gln Glu Ala Ser Leu Gln Ile Phe Asn
            835             840             845

Ile Lys Asp Tyr Asn Leu Asp Asn Leu Leu Glu Asn Pro Asn Lys Phe
        850             855             860

Asp Asp Glu Lys Tyr Trp Ile Thr Val Asp Thr Tyr Ser Ala Gln Gly
865             870             875             880

Glu Arg Ala Thr Ala Phe Ser Asn Thr Leu Asn Asn Ile Thr Ser Lys
                885             890             895

Tyr Trp Arg Val Val Phe Asp Thr Lys Gly Asp Arg Tyr Ser Ser Pro
            900             905             910

Val Val Pro Glu Leu Gln Ile Leu Gly Tyr Pro Leu Pro Asn Ala Asp
            915             920             925

Thr Ile Met Lys Thr Val Thr Thr Ala Lys Glu Leu Ser Gln Gln Lys
            930             935             940

Asp Lys Phe Ser Gln Lys Met Leu Asp Glu Leu Lys Ile Lys Glu Met
945             950             955             960

Ala Leu Glu Thr Ser Leu Asn Ser Lys Ile Phe Asp Val Thr Ala Ile
                965             970             975

Asn Ala Asn Ala Gly Val Leu Lys Asp Cys Ile Glu Lys Arg Gln Leu
            980             985             990

Leu Lys Lys
    995
```

UNITED STATES PATENT AND TRADEMARK OFFICE
CERTIFICATE OF CORRECTION

PATENT NO. : 11,001,819 B2  
APPLICATION NO. : 15/745357  
DATED : May 11, 2021  
INVENTOR(S) : Kawaguchi et al.

It is certified that error appears in the above-identified patent and that said Letters Patent is hereby corrected as shown below:

In the Claims

Column 70, Line 13, delete "D40 5A" and insert -- D405A --.

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*